United States Patent
Brady et al.

(10) Patent No.: US 11,464,622 B2
(45) Date of Patent: *Oct. 11, 2022

(54) TWO-PART ACCOMMODATING INTRAOCULAR LENS DEVICE

(71) Applicant: LensGen, Inc., Irvine, CA (US)

(72) Inventors: Daniel Brady, San Juan Capistrano, CA (US); Thomas Silvestrini, Alamo, CA (US); Ramgopal Rao, Irvine, CA (US)

(73) Assignee: LensGen, Inc., Irvine, CA (US)

( * ) Notice: Subject to any disclaimer, the term of this patent is extended or adjusted under 35 U.S.C. 154(b) by 33 days.

This patent is subject to a terminal disclaimer.

(21) Appl. No.: 16/694,968

(22) Filed: Nov. 25, 2019

(65) Prior Publication Data
US 2020/0085568 A1  Mar. 19, 2020

Related U.S. Application Data

(63) Continuation of application No. 16/207,658, filed on Dec. 3, 2018, now Pat. No. 11,000,364, which is a
(Continued)

(51) Int. Cl.
  *A61F 2/16* (2006.01)
  *A61B 90/00* (2016.01)
  *A61F 2/14* (2006.01)
(52) U.S. Cl.
  CPC ............ *A61F 2/1635* (2013.01); *A61B 90/06* (2016.02); *A61F 2/1648* (2013.01);
  (Continued)
(58) Field of Classification Search
  None
  See application file for complete search history.

(56) References Cited

U.S. PATENT DOCUMENTS

| 4,032,502 | A | 6/1977 | Lee et al. |
| 4,073,014 | A | 2/1978 | Poler |

(Continued)

FOREIGN PATENT DOCUMENTS

| CN | 1064611 | 9/1992 |
| CN | 102186438 | 9/2011 |

(Continued)

OTHER PUBLICATIONS

Extended European Search Report and Opinion dated Jan. 20, 20157 for EP Application No. 14857916.2. (9 pages).
(Continued)

*Primary Examiner* — Leslie Lopez
(74) *Attorney, Agent, or Firm* — Knobbe Martens Olson & Bear, LLP

(57) ABSTRACT

A two-part accommodating intraocular lens (IOL) device for implantation in a capsular bag of a patient's eye. The IOL device includes a primary lens assembly and a power changing lens. The primary lens assembly includes a fixed lens and a peripherally disposed centration member. The centration member has a circumferential distal edge and a first coupling surface adjacent the circumferential distal edge. The power changing lens has an enclosed, fluid- or gel-filled lens cavity and haptic system disposed peripherally of the lens cavity. The haptic system has a peripheral engaging edge configured to contact the capsular bag and a second coupling surface. The first and second coupling surfaces are in sliding contact with one another to permit movement of the power changing lens relative to the primary lens assembly and also to maintain a spaced relationship between the fixed lens and the lens cavity during radial compression of the power changing lens.

20 Claims, 14 Drawing Sheets

Related U.S. Application Data continuation of application No. 15/144,544, filed on May 2, 2016, now Pat. No. 10,159,564, which is a continuation of application No. PCT/US2014/063538, filed on Oct. 31, 2014.

(60) Provisional application No. 61/899,110, filed on Nov. 1, 2013.

(52) U.S. Cl.
CPC ............ *A61B 2090/061* (2016.02); *A61F 2/15* (2015.04); *A61F 2002/169* (2015.04); *A61F 2002/1682* (2015.04); *A61F 2002/16901* (2015.04); *A61F 2002/16902* (2015.04); *A61F 2250/0018* (2013.01)

(56) References Cited

U.S. PATENT DOCUMENTS

| | | |
|---|---|---|
| 4,118,808 A | 10/1978 | Poler |
| 4,373,218 A | 2/1983 | Schachar |
| 4,512,040 A | 4/1985 | McClure |
| 4,585,457 A | 4/1986 | Kalb |
| 4,676,791 A | 6/1987 | LeMaster et al. |
| 4,720,286 A | 1/1988 | Bailey et al. |
| 4,731,078 A | 3/1988 | Stoy et al. |
| 4,822,360 A | 4/1989 | Deacon |
| 4,842,601 A | 6/1989 | Smith |
| 4,882,368 A | 11/1989 | Elias et al. |
| 4,888,012 A | 12/1989 | Horn et al. |
| 4,892,543 A | 1/1990 | Turley |
| 4,932,966 A | 7/1990 | Christie et al. |
| 5,035,710 A | 7/1991 | Nakada et al. |
| 5,059,668 A | 10/1991 | Fukuda et al. |
| 5,074,876 A | 12/1991 | Kelman |
| 5,091,121 A | 2/1992 | Nakada et al. |
| 5,152,788 A | 10/1992 | Isaacson et al. |
| 5,167,883 A | 12/1992 | Takemasa et al. |
| 5,171,773 A | 12/1992 | Chaffe et al. |
| 5,227,447 A | 7/1993 | Sato et al. |
| 5,236,970 A | 8/1993 | Christ et al. |
| 5,264,522 A | 11/1993 | Mize et al. |
| 5,275,623 A | 1/1994 | Sarfarazi |
| 5,278,258 A | 1/1994 | Gerace et al. |
| 5,312,860 A | 5/1994 | Mize et al. |
| 5,326,506 A | 7/1994 | Vanderbilt |
| 5,336,487 A | 8/1994 | Refojo et al. |
| 5,443,506 A | 8/1995 | Garabet |
| 5,447,987 A | 9/1995 | Sato et al. |
| 5,489,302 A | 2/1996 | Skottun |
| 5,583,178 A | 12/1996 | Oxman et al. |
| 5,607,472 A | 3/1997 | Thompson |
| 5,665,794 A | 9/1997 | Maxson et al. |
| 5,854,310 A | 12/1998 | Maxson |
| 6,071,439 A | 6/2000 | Bawa et al. |
| 6,117,171 A | 9/2000 | Skottun |
| 6,197,057 B1 | 3/2001 | Peyman et al. |
| 6,200,342 B1 | 3/2001 | Tassignon |
| 6,200,581 B1 | 3/2001 | Lin et al. |
| 6,201,091 B1 | 3/2001 | Halloran et al. |
| 6,361,561 B1 | 3/2002 | Huo et al. |
| 6,551,354 B1 | 4/2003 | Ghazizadeh et al. |
| 6,616,691 B1 | 9/2003 | Tran |
| 6,695,881 B2 | 2/2004 | Peng et al. |
| 6,730,123 B1 | 5/2004 | Klopotek |
| 6,797,004 B1 | 9/2004 | Brady et al. |
| 6,836,374 B2 | 12/2004 | Esch et al. |
| 6,855,164 B2 | 2/2005 | Glazier |
| 6,858,040 B2 | 2/2005 | Nguyen et al. |
| 6,860,601 B2 | 3/2005 | Shadduck |
| 6,881,225 B2 | 4/2005 | Okada |
| 6,926,736 B2 | 8/2005 | Peng et al. |
| 6,930,838 B2 | 8/2005 | Schachar |
| 6,935,743 B2 | 8/2005 | Shadduck |
| 6,966,649 B2 | 11/2005 | Shadduck |
| 6,969,403 B2 | 11/2005 | Peng et al. |
| 6,991,651 B2 | 1/2006 | Portney |
| 7,041,134 B2 | 5/2006 | Nguyen et al. |
| 7,063,723 B2 | 6/2006 | Ran |
| 7,068,439 B2 | 6/2006 | Esch et al. |
| 7,122,053 B2 | 10/2006 | Esch |
| 7,150,760 B2 | 12/2006 | Zhang |
| 7,217,288 B2 | 5/2007 | Esch et al. |
| 7,220,279 B2 | 5/2007 | Nun |
| 7,223,288 B2 | 5/2007 | Zhang et al. |
| 7,226,478 B2 | 6/2007 | Ting et al. |
| 7,229,475 B2 | 6/2007 | Glazier |
| 7,238,201 B2 | 7/2007 | Portney et al. |
| 7,247,168 B2 | 7/2007 | Esch et al. |
| 7,261,737 B2 | 8/2007 | Esch et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,316,713 B2 | 1/2008 | Zhang |
| 7,416,562 B2 | 8/2008 | Gross |
| 7,438,723 B2 | 10/2008 | Esch |
| 7,452,377 B2 | 11/2008 | Watling et al. |
| 7,453,646 B2 | 11/2008 | Lo |
| 7,455,691 B2 | 11/2008 | Feingold et al. |
| 7,485,144 B2 | 2/2009 | Esch |
| 7,591,849 B2 | 9/2009 | Richardson |
| 7,637,947 B2 | 12/2009 | Smith et al. |
| 7,662,179 B2 | 2/2010 | Sarfarazi |
| 7,675,686 B2 | 3/2010 | Lo et al. |
| 7,753,953 B1 | 7/2010 | Yee |
| 7,776,088 B2 | 8/2010 | Shadduck |
| 7,780,729 B2 | 8/2010 | Nguyen et al. |
| 7,815,678 B2 | 10/2010 | Nun |
| 7,842,087 B2 | 11/2010 | Nun |
| 7,854,764 B2 | 12/2010 | Nun |
| 7,857,850 B2 | 12/2010 | Mentak et al. |
| 7,918,886 B2 | 4/2011 | Aharoni et al. |
| 7,981,155 B2 | 7/2011 | Cumming |
| 7,985,253 B2 | 7/2011 | Cumming |
| 7,986,465 B1 | 7/2011 | Lo et al. |
| 7,998,198 B2 | 8/2011 | Angelopoulos et al. |
| 7,998,199 B2 | 8/2011 | Nun |
| 8,012,204 B2 | 9/2011 | Weinschenk, III et al. |
| 8,018,658 B2 | 9/2011 | Lo |
| 8,034,106 B2 | 10/2011 | Mentak et al. |
| 8,034,107 B2 | 10/2011 | Stenger |
| 8,038,711 B2 | 10/2011 | Clarke |
| 8,048,155 B2 | 11/2011 | Shadduck |
| 8,052,752 B2 | 11/2011 | Woods et al. |
| 8,062,361 B2 | 11/2011 | Nguyen et al. |
| 8,066,768 B2 | 11/2011 | Werblin |
| 8,066,769 B2 | 11/2011 | Werblin |
| 8,070,806 B2 | 12/2011 | Khoury |
| 8,158,712 B2 | 4/2012 | Your |
| 8,182,531 B2 | 5/2012 | Hermans et al. |
| 8,187,325 B2 | 5/2012 | Zadno-Azizi et al. |
| 8,197,541 B2 | 6/2012 | Schedler |
| 8,216,306 B2 | 7/2012 | Coroneo |
| 8,246,679 B2 | 8/2012 | Nguyen et al. |
| 8,254,034 B1 | 8/2012 | Shields et al. |
| 8,257,827 B1 | 9/2012 | Shi et al. |
| 8,273,123 B2 | 9/2012 | Nun |
| 8,303,656 B2 | 11/2012 | Shadduck |
| 8,308,800 B2 | 11/2012 | Chu |
| 8,314,927 B2 | 11/2012 | Choi et al. |
| 8,320,049 B2 | 11/2012 | Huang et al. |
| 8,328,869 B2 | 12/2012 | Smiley et al. |
| 8,361,145 B2 | 1/2013 | Scholl et al. |
| 8,377,124 B2 | 2/2013 | Hong et al. |
| 8,377,125 B2 | 2/2013 | Kellan |
| 8,398,709 B2 | 3/2013 | Nun |
| 8,414,646 B2 | 4/2013 | De Juan, Jr. et al. |
| 8,425,597 B2 | 4/2013 | Glick et al. |
| 8,425,599 B2 | 4/2013 | Shadduck |
| 8,430,928 B2 | 4/2013 | Liao |
| 8,447,086 B2 | 5/2013 | Hildebrand et al. |
| 8,454,688 B2 | 6/2013 | Esch et al. |
| 8,475,529 B2 | 7/2013 | Clarke |

(56) References Cited

U.S. PATENT DOCUMENTS

| | | |
|---|---|---|
| 8,491,651 B2 | 7/2013 | Tsai et al. |
| 8,496,701 B2 | 7/2013 | Hermans et al. |
| 8,500,806 B1 | 8/2013 | Phillips |
| 8,518,026 B2 | 8/2013 | Culbertson et al. |
| 8,545,556 B2 | 10/2013 | Woods et al. |
| 8,579,972 B2 | 11/2013 | Rombach |
| 8,585,758 B2 | 11/2013 | Woods |
| 8,603,167 B2 | 12/2013 | Rombach |
| 8,608,799 B2 | 12/2013 | Blake |
| 8,608,800 B2 | 12/2013 | Portney |
| 8,613,766 B2 | 12/2013 | Richardson et al. |
| 8,647,384 B2 | 2/2014 | Lu |
| 8,657,810 B2 | 2/2014 | Culbertson et al. |
| 8,657,878 B2 | 2/2014 | Mentak et al. |
| 8,668,734 B2 | 3/2014 | Hildebrand et al. |
| 8,690,942 B2 | 3/2014 | Hildebrand et al. |
| 8,715,345 B2 | 5/2014 | DeBoer et al. |
| 8,715,346 B2 | 5/2014 | De Juan, Jr. et al. |
| 8,734,509 B2 | 5/2014 | Mentak et al. |
| 8,771,347 B2 | 7/2014 | DeBoer et al. |
| 8,814,934 B2 | 8/2014 | Geraghty et al. |
| 8,834,565 B2 | 9/2014 | Nun |
| 8,834,566 B1 | 9/2014 | Jones |
| 8,858,626 B2 | 10/2014 | Noy |
| 8,867,141 B2 | 10/2014 | Pugh et al. |
| 8,900,298 B2 | 12/2014 | Anvar et al. |
| 8,900,300 B1 | 12/2014 | Wortz |
| 8,920,495 B2 | 12/2014 | Mirlay |
| 8,956,408 B2 | 2/2015 | Smiley et al. |
| 8,968,396 B2 | 3/2015 | Matthews et al. |
| 8,968,399 B2 | 3/2015 | Ghabra |
| 8,992,609 B2 | 3/2015 | Shadduck |
| 9,005,282 B2 | 4/2015 | Chang et al. |
| 9,005,283 B2 | 4/2015 | Nguyen et al. |
| 9,034,035 B2 | 5/2015 | Betser et al. |
| 9,044,317 B2 | 6/2015 | Hildebrand et al. |
| 9,072,600 B2 | 7/2015 | Tran |
| 9,090,033 B2 | 7/2015 | Carson et al. |
| 9,095,424 B2 | 8/2015 | Kahook et al. |
| 9,125,736 B2 | 9/2015 | Kahook et al. |
| 9,149,356 B2 | 10/2015 | Sarfarazi |
| 9,186,244 B2 | 11/2015 | Silvestrini et al. |
| 9,198,752 B2 | 12/2015 | Woods |
| 9,277,987 B2 | 3/2016 | Smiley et al. |
| 9,277,988 B1 | 3/2016 | Chu |
| 9,289,287 B2 | 3/2016 | Kahook et al. |
| 9,326,846 B2 | 5/2016 | Devita Gerardi et al. |
| 9,333,072 B2 | 5/2016 | Ichikawa |
| 9,358,103 B1 | 6/2016 | Wortz et al. |
| 9,364,316 B1 | 6/2016 | Kahook et al. |
| 9,387,069 B2 | 7/2016 | Kahook et al. |
| 9,398,949 B2 | 7/2016 | Werblin |
| 9,421,088 B1 | 8/2016 | Kahook et al. |
| 9,427,312 B2 | 8/2016 | DeBoer et al. |
| 9,433,497 B2 | 9/2016 | DeBoer et al. |
| 9,456,895 B2 | 10/2016 | Shadduck |
| 9,486,311 B2 | 11/2016 | Argento et al. |
| 9,610,155 B2 | 4/2017 | Matthews |
| 9,622,852 B2 | 4/2017 | Simonov et al. |
| 9,629,712 B2 | 4/2017 | Stenger |
| 9,636,213 B2 | 5/2017 | Brady |
| 9,655,716 B2 | 5/2017 | Cumming |
| 9,681,946 B2 | 6/2017 | Kahook et al. |
| 9,693,858 B2 | 7/2017 | Hildebrand et al. |
| 9,713,526 B2 | 7/2017 | Rombach |
| 9,713,527 B2 | 7/2017 | Nishi et al. |
| 9,717,589 B2 | 8/2017 | Simonov et al. |
| 9,744,027 B2 | 8/2017 | Jansen |
| 9,744,028 B2 | 8/2017 | Simonov et al. |
| 9,795,472 B2 | 10/2017 | Culbertson et al. |
| 9,795,473 B2 | 10/2017 | Smiley et al. |
| 9,808,339 B2 | 11/2017 | Dorronsoro Diaz et al. |
| 9,814,568 B2 | 11/2017 | Ben Nun |
| 9,814,570 B2 | 11/2017 | Robert et al. |
| 9,820,849 B2 | 11/2017 | Jansen |
| 9,848,980 B2 | 12/2017 | McCafferty |
| 9,855,137 B2 | 1/2018 | Smiley et al. |
| 9,855,139 B2 | 1/2018 | Matthews et al. |
| 9,861,469 B2 | 1/2018 | Simonov et al. |
| 9,872,762 B2 | 1/2018 | Scholl et al. |
| 9,872,763 B2 | 1/2018 | Smiley et al. |
| 9,877,825 B2 | 1/2018 | Kahook et al. |
| 9,883,940 B2 | 2/2018 | Nishi et al. |
| 9,925,039 B2 | 3/2018 | Sohn et al. |
| 9,925,040 B2 | 3/2018 | Kahook et al. |
| 9,931,202 B2 | 4/2018 | Borja et al. |
| 9,987,126 B2 | 6/2018 | Borja et al. |
| 10,004,596 B2 | 6/2018 | Brady et al. |
| 10,010,405 B2 | 7/2018 | Hayes |
| 10,028,824 B2 | 7/2018 | Kahook et al. |
| 10,039,635 B2 | 8/2018 | Wanders |
| 10,045,844 B2 | 8/2018 | Smiley et al. |
| 10,080,648 B2 | 9/2018 | Kahook et al. |
| 10,080,649 B2 | 9/2018 | Zhang et al. |
| 10,111,745 B2 | 10/2018 | Silvestrini et al. |
| 10,159,562 B2 | 12/2018 | Cady |
| 10,159,564 B2 | 12/2018 | Brady et al. |
| 10,195,017 B2 | 2/2019 | Culbertson et al. |
| 10,195,018 B2 | 2/2019 | Salahieh et al. |
| 10,195,020 B2 | 2/2019 | Matthews |
| 10,285,805 B2 | 5/2019 | De Juan, Jr. et al. |
| 10,299,910 B2 | 5/2019 | Cady |
| 10,299,913 B2 | 5/2019 | Smiley et al. |
| 10,327,886 B2 | 6/2019 | Sohn et al. |
| 10,350,056 B2 | 7/2019 | Argento et al. |
| 10,363,129 B2 | 7/2019 | Ghabra et al. |
| 10,368,979 B2 | 8/2019 | Scholl et al. |
| 10,390,937 B2 | 8/2019 | Smiley et al. |
| 10,433,949 B2 | 10/2019 | Smiley et al. |
| 10,463,473 B2 | 11/2019 | Rombach et al. |
| 10,485,654 B2 | 11/2019 | Brady et al. |
| 10,526,353 B2 | 1/2020 | Silvestrini |
| 10,548,719 B2 | 2/2020 | Pallikaris et al. |
| 10,647,831 B2 | 5/2020 | Silvestrini et al. |
| 10,772,721 B2 | 9/2020 | Rao et al. |
| 10,842,614 B2 | 11/2020 | Cady |
| 10,842,616 B2 | 11/2020 | Silvestrini et al. |
| 10,888,219 B2 | 1/2021 | Smith et al. |
| 10,905,547 B2 | 2/2021 | Auld et al. |
| 10,912,676 B2 | 2/2021 | Schaller et al. |
| 10,917,543 B2 | 2/2021 | Luna et al. |
| 10,945,832 B2 | 3/2021 | Cady |
| 10,959,836 B2 | 3/2021 | Qureshi et al. |
| 10,980,629 B2 | 4/2021 | Anvar et al. |
| 10,987,183 B2 | 4/2021 | Brennan et al. |
| 11,000,363 B2 | 5/2021 | Campin et al. |
| 11,000,367 B2 | 5/2021 | Wu et al. |
| 11,026,838 B2 | 6/2021 | Raksi |
| 11,039,901 B2 | 6/2021 | Tripathi |
| 11,040,477 B2 | 6/2021 | Chauvin et al. |
| 11,045,309 B2 | 6/2021 | Kahook et al. |
| 11,046,490 B2 | 6/2021 | Cerveny |
| 11,051,884 B2 | 7/2021 | Tripathi et al. |
| 11,065,107 B2 | 7/2021 | Brady et al. |
| 11,065,109 B2 | 7/2021 | Argento et al. |
| 11,065,152 B2 | 7/2021 | Kelleher et al. |
| 11,071,449 B2 | 7/2021 | Heeren |
| 11,071,622 B2 | 7/2021 | Matthews |
| 11,076,948 B2 | 8/2021 | Kahook et al. |
| 11,083,567 B2 | 8/2021 | Honigsbaum |
| 11,109,957 B2 | 9/2021 | Cady |
| 11,109,960 B2 | 9/2021 | Borja et al. |
| 11,110,005 B2 | 9/2021 | Diao et al. |
| 11,111,055 B2 | 9/2021 | Reece et al. |
| 11,141,263 B2 | 10/2021 | Argento et al. |
| 11,162,065 B2 | 11/2021 | Fachin et al. |
| 11,166,808 B2 | 11/2021 | Smiley et al. |
| 11,166,844 B2 | 11/2021 | Charles |
| 11,173,008 B2 | 11/2021 | Mirsepassi et al. |
| 11,213,606 B2 | 1/2022 | Jiang et al. |
| 11,224,540 B2 | 1/2022 | Sivadas |
| 11,298,221 B2 | 4/2022 | McCulloch |
| 2002/0005344 A1 | 1/2002 | Heidlas et al. |
| 2002/0055776 A1 | 5/2002 | Juan, Jr. et al. |

(56) References Cited

U.S. PATENT DOCUMENTS

| | | |
|---|---|---|
| 2002/0071856 A1 | 6/2002 | Dillingham et al. |
| 2002/0120329 A1 | 8/2002 | Lang et al. |
| 2002/0138140 A1 | 9/2002 | Hanna |
| 2003/0060881 A1 | 3/2003 | Glick et al. |
| 2003/0093149 A1 | 5/2003 | Glazier |
| 2003/0105522 A1 | 6/2003 | Glazier |
| 2003/0109926 A1 | 6/2003 | Portney |
| 2003/0149480 A1 | 8/2003 | Shadduck |
| 2003/0158295 A1 | 8/2003 | Fukuda et al. |
| 2003/0204254 A1 | 10/2003 | Peng et al. |
| 2003/0204256 A1 | 10/2003 | Peng et al. |
| 2004/0015236 A1 | 1/2004 | Sarfarazi |
| 2004/0082993 A1* | 4/2004 | Woods .................. A61F 2/1635 623/6.28 |
| 2004/0082994 A1 | 4/2004 | Woods et al. |
| 2004/0111152 A1 | 6/2004 | Kelman |
| 2004/0148023 A1 | 7/2004 | Shu |
| 2004/0162612 A1 | 8/2004 | Portney et al. |
| 2004/0169816 A1 | 9/2004 | Esch |
| 2004/0169932 A1 | 9/2004 | Esch et al. |
| 2004/0249455 A1 | 12/2004 | Tran |
| 2005/0021139 A1 | 1/2005 | Shadduck |
| 2005/0071002 A1 | 3/2005 | Glazier |
| 2005/0107873 A1 | 5/2005 | Zhou |
| 2005/0119740 A1 | 6/2005 | Esch et al. |
| 2005/0137703 A1 | 6/2005 | Chen |
| 2005/0149183 A1 | 7/2005 | Shadduck |
| 2005/0251253 A1 | 11/2005 | Gross |
| 2005/0251254 A1 | 11/2005 | Brady et al. |
| 2005/0267575 A1 | 12/2005 | Nguyen et al. |
| 2006/0041307 A1 | 2/2006 | Esch et al. |
| 2006/0047339 A1 | 3/2006 | Brown |
| 2006/0069178 A1 | 3/2006 | Rastogi et al. |
| 2006/0074487 A1 | 4/2006 | Gilg |
| 2006/0100701 A1 | 5/2006 | Esch et al. |
| 2006/0111776 A1 | 5/2006 | Glick et al. |
| 2006/0134173 A1 | 6/2006 | Liu et al. |
| 2006/0135477 A1 | 6/2006 | Haitjema et al. |
| 2006/0212116 A1 | 9/2006 | Woods |
| 2006/0238702 A1 | 10/2006 | Glick et al. |
| 2006/0241752 A1 | 10/2006 | Israel |
| 2006/0271186 A1 | 11/2006 | Nishi et al. |
| 2007/0016293 A1 | 1/2007 | Tran |
| 2007/0032868 A1 | 2/2007 | Woods |
| 2007/0050024 A1 | 3/2007 | Zhang |
| 2007/0050025 A1 | 3/2007 | Nguyen et al. |
| 2007/0078515 A1 | 4/2007 | Brady et al. |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0118216 A1 | 5/2007 | Pynson |
| 2007/0129798 A1 | 6/2007 | Chawdhary |
| 2007/0129799 A1 | 6/2007 | Schedler |
| 2007/0129800 A1 | 6/2007 | Cumming |
| 2007/0129801 A1 | 6/2007 | Cumming |
| 2007/0132949 A1 | 6/2007 | Phelan |
| 2007/0156236 A1 | 7/2007 | Stenger |
| 2007/0213817 A1 | 9/2007 | Esch et al. |
| 2007/0260308 A1 | 11/2007 | Tran |
| 2007/0260310 A1 | 11/2007 | Richardson |
| 2008/0015689 A1 | 1/2008 | Esch et al. |
| 2008/0033547 A1 | 2/2008 | Chang et al. |
| 2008/0046074 A1 | 2/2008 | Smith et al. |
| 2008/0046075 A1 | 2/2008 | Esch et al. |
| 2008/0046077 A1 | 2/2008 | Cumming |
| 2008/0051886 A1 | 2/2008 | Lin |
| 2008/0154364 A1 | 6/2008 | Richardson et al. |
| 2008/0200982 A1 | 8/2008 | Your |
| 2008/0269887 A1 | 10/2008 | Cumming |
| 2008/0300680 A1 | 12/2008 | Nun |
| 2008/0306587 A1 | 12/2008 | Your |
| 2008/0306588 A1* | 12/2008 | Smiley .................. A61F 2/1635 623/6.13 |
| 2008/0306589 A1 | 12/2008 | Donitzky et al. |
| 2009/0005865 A1 | 1/2009 | Smiley et al. |
| 2009/0027661 A1 | 1/2009 | Choi et al. |
| 2009/0043384 A1 | 2/2009 | Niwa et al. |
| 2009/0116118 A1 | 5/2009 | Frazier et al. |
| 2009/0125106 A1 | 5/2009 | Weinschenk, III et al. |
| 2009/0149952 A1 | 6/2009 | Shadduck |
| 2009/0198326 A1 | 8/2009 | Zhou et al. |
| 2009/0204209 A1 | 8/2009 | Tran |
| 2009/0204210 A1 | 8/2009 | Pynson |
| 2009/0264998 A1 | 10/2009 | Mentak et al. |
| 2009/0292355 A1 | 11/2009 | Boyd et al. |
| 2009/0319040 A1 | 12/2009 | Khoury |
| 2010/0004742 A1 | 1/2010 | Cumming |
| 2010/0055449 A1 | 3/2010 | Ota |
| 2010/0057095 A1 | 3/2010 | Khuray et al. |
| 2010/0094412 A1 | 4/2010 | Wensrich |
| 2010/0094413 A1 | 4/2010 | Rombach et al. |
| 2010/0131058 A1 | 5/2010 | Shadduck |
| 2010/0131059 A1 | 5/2010 | Callahan et al. |
| 2010/0179653 A1 | 7/2010 | Argento et al. |
| 2010/0204787 A1 | 8/2010 | Noy |
| 2010/0211169 A1 | 8/2010 | Stanley et al. |
| 2010/0228344 A1 | 9/2010 | Shadduck |
| 2010/0288346 A1 | 9/2010 | Esch |
| 2010/0324672 A1 | 12/2010 | Esch et al. |
| 2010/0324674 A1 | 12/2010 | Brown |
| 2011/0029074 A1 | 2/2011 | Reisin et al. |
| 2011/0071628 A1 | 3/2011 | Gross et al. |
| 2011/0118834 A1 | 5/2011 | Lo et al. |
| 2011/0118836 A1 | 5/2011 | Jain |
| 2011/0208301 A1 | 8/2011 | Anvar et al. |
| 2011/0224788 A1 | 9/2011 | Webb |
| 2011/0264209 A1 | 10/2011 | Wiechmann et al. |
| 2011/0282442 A1 | 11/2011 | Scholl et al. |
| 2011/0288638 A1 | 11/2011 | Smiley et al. |
| 2012/0016473 A1 | 1/2012 | Brady et al. |
| 2012/0035724 A1 | 2/2012 | Clarke |
| 2012/0071972 A1 | 3/2012 | Zhao |
| 2012/0078364 A1 | 3/2012 | Stenger |
| 2012/0095125 A1 | 4/2012 | Hu et al. |
| 2012/0150292 A1 | 6/2012 | Mentak et al. |
| 2012/0232649 A1 | 9/2012 | Cuevas |
| 2012/0245683 A1 | 9/2012 | Christie et al. |
| 2012/0253458 A1 | 10/2012 | Geraghty et al. |
| 2012/0253459 A1 | 10/2012 | Reich et al. |
| 2012/0290084 A1 | 11/2012 | Coroneo |
| 2012/0296423 A1 | 11/2012 | Caffey |
| 2012/0296424 A1 | 11/2012 | Betser |
| 2012/0310341 A1 | 12/2012 | Simonov et al. |
| 2012/0310343 A1 | 12/2012 | Van Noy |
| 2013/0006353 A1 | 1/2013 | Betser et al. |
| 2013/0035760 A1 | 2/2013 | Portney |
| 2013/0038944 A1 | 2/2013 | Chang et al. |
| 2013/0040073 A1 | 2/2013 | Pett et al. |
| 2013/0060331 A1 | 3/2013 | Shadduck |
| 2013/0110234 A1 | 5/2013 | DeVita et al. |
| 2013/0110235 A1 | 5/2013 | Shweigerling |
| 2013/0116781 A1 | 5/2013 | Nun |
| 2013/0131794 A1 | 5/2013 | Smiley et al. |
| 2013/0190867 A1 | 7/2013 | Peyman |
| 2013/0231741 A1 | 9/2013 | Clarke |
| 2013/0250239 A1 | 9/2013 | Hildebrand et al. |
| 2013/0268070 A1 | 10/2013 | Esch et al. |
| 2013/0297018 A1 | 11/2013 | Brady et al. |
| 2013/0317607 A1 | 11/2013 | DeBoer et al. |
| 2013/0317608 A1 | 11/2013 | Hermans et al. |
| 2014/0012277 A1 | 1/2014 | Matthews et al. |
| 2014/0058507 A1 | 2/2014 | Reich et al. |
| 2014/0085726 A1 | 3/2014 | Portney |
| 2014/0100654 A1 | 4/2014 | Portney et al. |
| 2014/0107459 A1 | 4/2014 | Lind et al. |
| 2014/0111765 A1 | 4/2014 | DeBoer et al. |
| 2014/0121768 A1 | 5/2014 | Simpson |
| 2014/0135917 A1 | 5/2014 | Glazier |
| 2014/0135918 A1 | 5/2014 | De Juan, Jr. et al. |
| 2014/0142558 A1 | 5/2014 | Culbertson et al. |
| 2014/0172089 A1 | 6/2014 | Lee et al. |
| 2014/0172092 A1 | 6/2014 | Carson et al. |
| 2014/0180403 A1 | 6/2014 | Silvestrini et al. |
| 2014/0180404 A1 | 6/2014 | Tram |

(56) References Cited

U.S. PATENT DOCUMENTS

| | | |
|---|---|---|
| 2014/0180405 A1 | 6/2014 | Weinschenk, III et al. |
| 2014/0180406 A1 | 6/2014 | Simpson |
| 2014/0180407 A1 | 6/2014 | Sohn et al. |
| 2014/0180410 A1 | 6/2014 | Gerardi |
| 2014/0227437 A1 | 8/2014 | DeBoer et al. |
| 2014/0228949 A1 | 8/2014 | Argento et al. |
| 2014/0249625 A1 | 9/2014 | Shadduck |
| 2014/0257478 A1 | 9/2014 | McCafferty |
| 2014/0257479 A1 | 9/2014 | McCafferty |
| 2014/0296977 A1 | 10/2014 | Culbertson et al. |
| 2014/0309734 A1 | 10/2014 | Sohn et al. |
| 2015/0087743 A1 | 3/2015 | Anvar et al. |
| 2015/0105760 A1 | 4/2015 | Rao et al. |
| 2015/0127102 A1 | 5/2015 | Wortz |
| 2015/0173892 A1 | 6/2015 | Borja et al. |
| 2015/0202041 A1 | 7/2015 | Shadduck |
| 2015/0216652 A1 | 8/2015 | Jansen |
| 2015/0230980 A1 | 8/2015 | Culbertson et al. |
| 2015/0238310 A1 | 8/2015 | Matthews et al. |
| 2015/0327991 A1 | 11/2015 | Hayes |
| 2015/0342728 A1 | 12/2015 | Simonov et al. |
| 2015/0359625 A1 | 12/2015 | Argal et al. |
| 2015/0366656 A1 | 12/2015 | Wortz et al. |
| 2016/0000558 A1 | 1/2016 | Honigsbaum |
| 2016/0008126 A1 | 1/2016 | Salahieh et al. |
| 2016/0051361 A1 | 2/2016 | Phillips |
| 2016/0058553 A1 | 3/2016 | Salahieh et al. |
| 2016/0074154 A1 | 3/2016 | Woods |
| 2016/0106534 A1 | 4/2016 | Deboer et al. |
| 2016/0113761 A1 | 4/2016 | Nishi et al. |
| 2016/0128826 A1 | 5/2016 | Silvestrini et al. |
| 2016/0184089 A1 | 6/2016 | Dudee et al. |
| 2016/0184092 A1 | 6/2016 | Smiley et al. |
| 2016/0208138 A1 | 7/2016 | Nishijima et al. |
| 2016/0256265 A1 | 9/2016 | Borja et al. |
| 2016/0262875 A1 | 9/2016 | Smith et al. |
| 2016/0281019 A1 | 9/2016 | Deklippel et al. |
| 2016/0287380 A1 | 10/2016 | Shi et al. |
| 2016/0317287 A1 | 11/2016 | Silvestrini et al. |
| 2016/0361157 A1 | 12/2016 | Honigsbaum |
| 2017/0020662 A1 | 1/2017 | Shadduck |
| 2017/0049561 A1 | 2/2017 | Smiley et al. |
| 2017/0049562 A1 | 2/2017 | Argento et al. |
| 2017/0100234 A1 | 4/2017 | Culbertson et al. |
| 2017/0216021 A1 | 8/2017 | Brady |
| 2017/0247525 A1 | 8/2017 | Silvestrini et al. |
| 2017/0290658 A1 | 10/2017 | Hildebrand et al. |
| 2017/0319332 A1 | 11/2017 | Kahook et al. |
| 2017/0348095 A1 | 12/2017 | Wortz et al. |
| 2018/0014928 A1 | 1/2018 | Kahook et al. |
| 2018/0028308 A1 | 2/2018 | Smiley et al. |
| 2018/0085211 A1 | 3/2018 | Culbertson et al. |
| 2018/0110613 A1 | 4/2018 | Wortz et al. |
| 2018/0125640 A1 | 5/2018 | Smiley et al. |
| 2018/0132997 A1 | 5/2018 | Smiley et al. |
| 2018/0147051 A1 | 5/2018 | Scholl et al. |
| 2018/0153682 A1 | 6/2018 | Hajela et al. |
| 2018/0161152 A1 | 6/2018 | Argento et al. |
| 2018/0161153 A1 | 6/2018 | Kahook et al. |
| 2018/0177589 A1 | 6/2018 | Argento et al. |
| 2018/0177639 A1 | 6/2018 | Rao et al. |
| 2018/0185139 A1 | 7/2018 | Sohn et al. |
| 2018/0256315 A1 | 9/2018 | Hildebrand et al. |
| 2018/0271642 A1 | 9/2018 | Wortz et al. |
| 2018/0271645 A1 | 9/2018 | Brady et al. |
| 2018/0280135 A1 | 10/2018 | Otts |
| 2018/0296323 A1 | 10/2018 | Olcina Portilla |
| 2018/0307061 A1 | 10/2018 | State et al. |
| 2018/0318068 A1 | 11/2018 | Otts et al. |
| 2018/0344453 A1 | 12/2018 | Brady |
| 2018/0360659 A1 | 12/2018 | Culbertson et al. |
| 2018/0368971 A1 | 12/2018 | Zacher et al. |
| 2018/0368973 A1 | 12/2018 | Wortz et al. |
| 2018/0368974 A1 | 12/2018 | Kahook et al. |
| 2019/0000612 A1 | 1/2019 | Rao et al. |
| 2019/0015198 A1 | 1/2019 | Kuiper |
| 2019/0021848 A1 | 1/2019 | Kahook et al. |
| 2019/0069989 A1 | 3/2019 | Otts et al. |
| 2019/0076239 A1 | 3/2019 | Wortz et al. |
| 2019/0076241 A1 | 3/2019 | Alarcon Heredia et al. |
| 2019/0076243 A1 | 3/2019 | Hadba et al. |
| 2019/0083235 A1 | 3/2019 | Wortz |
| 2019/0099263 A1 | 4/2019 | Brady et al. |
| 2019/0269499 A1 | 9/2019 | Ellis |
| 2019/0269500 A1 | 9/2019 | De Juan, Jr. et al. |
| 2019/0274823 A1 | 9/2019 | Argento et al. |
| 2019/0358025 A1 | 11/2019 | Smiley et al. |
| 2019/0374333 A1 | 12/2019 | Shadduck |
| 2019/0374334 A1 | 12/2019 | Brady et al. |
| 2020/0000577 A1 | 1/2020 | Smiley et al. |
| 2020/0054445 A1 | 2/2020 | Rosen et al. |
| 2020/0129287 A1 | 4/2020 | Culbertson et al. |
| 2020/0138564 A1 | 5/2020 | Culbertson et al. |
| 2020/0157124 A1 | 5/2020 | Silvestrini |
| 2020/0179104 A1 | 6/2020 | Brady et al. |
| 2020/0261217 A1 | 8/2020 | Dudee |
| 2020/0337833 A1 | 10/2020 | Green |
| 2020/0345481 A1 | 11/2020 | Ellis |
| 2020/0369853 A1 | 11/2020 | Silvestrini et al. |
| 2020/0397562 A1 | 12/2020 | Cady |
| 2021/0007554 A1 | 1/2021 | Byun et al. |
| 2021/0015303 A1 | 1/2021 | Byun et al. |
| 2021/0015359 A1 | 1/2021 | Goldshleger et al. |
| 2021/0030530 A1 | 2/2021 | Smiley et al. |
| 2021/0038373 A1 | 2/2021 | Collins et al. |
| 2021/0063767 A1 | 3/2021 | Hong et al. |
| 2021/0093447 A1 | 4/2021 | Heckler et al. |
| 2021/0100649 A1 | 4/2021 | Smiley |
| 2021/0100650 A1 | 4/2021 | Smiley et al. |
| 2021/0100652 A1 | 4/2021 | Walz et al. |
| 2021/0113327 A1 | 4/2021 | Auld et al. |
| 2021/0128195 A1 | 5/2021 | Abt |
| 2021/0128516 A1 | 5/2021 | Cheng et al. |
| 2021/0128800 A1 | 5/2021 | Chon et al. |
| 2021/0154957 A1 | 5/2021 | Olson et al. |
| 2021/0191153 A1 | 6/2021 | Borja et al. |
| 2021/0191154 A1 | 6/2021 | Borja et al. |
| 2021/0196890 A1 | 7/2021 | Appy et al. |
| 2021/0196893 A1 | 7/2021 | Appy et al. |
| 2021/0196894 A1 | 7/2021 | Appy et al. |
| 2021/0196900 A1 | 7/2021 | Appy et al. |
| 2021/0205134 A1 | 7/2021 | Rao et al. |
| 2021/0220067 A1 | 7/2021 | Charles |
| 2021/0228333 A1 | 7/2021 | Hubschman et al. |
| 2021/0244488 A1 | 8/2021 | Carbone et al. |
| 2021/0251718 A1 | 8/2021 | Tripathi |
| 2021/0259827 A1 | 8/2021 | Brady et al. |
| 2021/0282920 A1 | 9/2021 | Cady |
| 2021/0284944 A1 | 9/2021 | Grandhi et al. |
| 2021/0290369 A1 | 9/2021 | Cady |
| 2021/0290370 A1 | 9/2021 | Cady |
| 2021/0290371 A1 | 9/2021 | Anvar et al. |
| 2021/0290374 A1 | 9/2021 | Kahook et al. |
| 2021/0291469 A1 | 9/2021 | Zheng et al. |
| 2021/0292557 A1 | 9/2021 | Cheng et al. |
| 2021/0292558 A1 | 9/2021 | Bassampour et al. |
| 2021/0297560 A1 | 9/2021 | Luna et al. |
| 2021/0302625 A1 | 9/2021 | Cheng et al. |
| 2021/0315688 A1 | 10/2021 | Matthews |
| 2021/0322151 A1 | 10/2021 | Kahook et al. |
| 2021/0322219 A1 | 10/2021 | Raksi |
| 2021/0361415 A1 | 11/2021 | Borja et al. |
| 2021/0369106 A1 | 12/2021 | Campin et al. |
| 2021/0369446 A1 | 12/2021 | Taber et al. |
| 2021/0371150 A1 | 12/2021 | Leibold et al. |
| 2021/0401570 A1 | 12/2021 | Brady et al. |
| 2022/0000606 A1 | 1/2022 | Cady |
| 2022/0015946 A1 | 1/2022 | Hallen et al. |
| 2022/0047383 A1 | 2/2022 | Brady et al. |

FOREIGN PATENT DOCUMENTS

| | | |
|---|---|---|
| CN | 102271623 | 12/2011 |
| DE | 20 2010 003217 U1 | 8/2011 |

(56) References Cited

FOREIGN PATENT DOCUMENTS

| | | |
|---|---|---|
| EP | 0356050 A1 | 2/1990 |
| EP | 0766540 B1 | 8/1999 |
| EP | 1 852 090 | 1/2009 |
| EP | 1 859 760 | 4/2010 |
| EP | 2 451 380 | 3/2014 |
| EP | 2 473 137 | 3/2014 |
| EP | 2 111 822 | 8/2014 |
| EP | 1881818 B1 | 7/2015 |
| EP | 2 512 374 | 11/2015 |
| EP | 2 501 336 | 9/2016 |
| EP | 3 049 023 | 6/2017 |
| EP | 3 035 889 | 2/2019 |
| EP | 3 171 821 | 3/2020 |
| EP | 3 463 186 | 8/2020 |
| EP | 3 003 217 | 10/2020 |
| EP | 3 782 584 | 2/2021 |
| EP | 3 651 693 | 5/2021 |
| EP | 3 197 396 | 9/2021 |
| EP | 3 888 595 | 10/2021 |
| EP | 3 932 367 | 1/2022 |
| EP | 3946 155 | 2/2022 |
| JP | H09-150002 A | 6/1997 |
| JP | 2005-511201 | 4/2005 |
| JP | 2006-511245 | 4/2006 |
| JP | 2006-516002 | 6/2006 |
| JP | 2007-313326 | 12/2007 |
| JP | 2010-514507 | 5/2010 |
| JP | 2011-526822 | 10/2011 |
| JP | 2013-047290 | 3/2013 |
| WO | WO 92/17132 | 10/1992 |
| WO | WO 99/29266 | 6/1999 |
| WO | WO 1999/056670 | 11/1999 |
| WO | WO 2000/021467 | 4/2000 |
| WO | WO 2001/034067 | 5/2001 |
| WO | WO 2004/037127 | 5/2004 |
| WO | WO 2004/052242 | 6/2004 |
| WO | WO 2004/054471 | 7/2004 |
| WO | WO 2004/072689 | 8/2004 |
| WO | WO 2006/047383 | 5/2006 |
| WO | WO 2007/005778 | 1/2007 |
| WO | WO 2007/047529 | 4/2007 |
| WO | WO 2007/047530 | 4/2007 |
| WO | WO 2008/024766 | 2/2008 |
| WO | WO 2008/031231 | 3/2008 |
| WO | WO 2008/077040 | 6/2008 |
| WO | WO 2008/082957 | 7/2008 |
| WO | WO 2008/103798 | 8/2008 |
| WO | WO 2009/015161 | 1/2009 |
| WO | WO 2009/015226 | 1/2009 |
| WO | WO 2009/015234 | 1/2009 |
| WO | WO 2009/015240 | 1/2009 |
| WO | WO 2009/064876 | 5/2009 |
| WO | WO 2010/010565 | 1/2010 |
| WO | WO 2010/081093 | 7/2010 |
| WO | WO 2011/026068 | 3/2011 |
| WO | WO 2011/106435 | 9/2011 |
| WO | WO 2011/137191 | 11/2011 |
| WO | WO 2012/006616 | 1/2012 |
| WO | WO 2012/129407 | 9/2012 |
| WO | WO 2013/016804 | 2/2013 |
| WO | WO 2013/070924 | 5/2013 |
| WO | WO 2013/142323 | 9/2013 |
| WO | WO 2013/166068 | 11/2013 |
| WO | WO 2013/180254 | 12/2013 |
| WO | WO 2013/190130 | 12/2013 |
| WO | WO 2014/099630 | 6/2014 |
| WO | WO 2014/145562 | 9/2014 |
| WO | WO 2014/152017 | 9/2014 |
| WO | WO 2014/197170 | 12/2014 |
| WO | WO 2015/066502 | 5/2015 |
| WO | WO 2015/066532 | 5/2015 |
| WO | WO 2015/126604 | 8/2015 |
| WO | WO 2015/148673 | 10/2015 |
| WO | WO 2016/018932 | 2/2016 |
| WO | WO 2016/033217 | 3/2016 |
| WO | WO 2016/049059 | 3/2016 |
| WO | WO 2016/122805 | 8/2016 |
| WO | WO 2016/201351 | 12/2016 |
| WO | WO 2017/079449 | 5/2017 |
| WO | WO 2017/079733 | 5/2017 |
| WO | WO 2017/087358 | 5/2017 |
| WO | WO 2017/096087 | 6/2017 |
| WO | WO 2017/192855 | 11/2017 |
| WO | WO 2017/205811 | 11/2017 |
| WO | WO 2018/081595 | 5/2018 |
| WO | WO 2018/119408 | 6/2018 |
| WO | WO 2018/167099 | 9/2018 |
| WO | WO 2018/222579 | 12/2018 |
| WO | WO 2018/227014 | 12/2018 |
| WO | WO 2019/005859 | 1/2019 |
| WO | WO 2019/027845 | 2/2019 |
| WO | WO 2019/089515 | 5/2019 |
| WO | WO 2019/236908 | 12/2019 |
| WO | WO 2021/092222 | 5/2021 |
| WO | WO 2021/119174 | 6/2021 |
| WO | WO 2021/126451 | 6/2021 |

OTHER PUBLICATIONS

International Search Report and Written Opinion dated Feb. 11, 2015 for PCT/US2014/063538. (6 pages).

Aliancy, et al., "Long-term capsule clarity with a disk-shaped intraocular lens", Journal of Cataract & Refractive Surgery, Apr. 2018, vol. 44, Issue 4, pp. 504-509.

Ehrmann, et al., "Biomechanical analysis of the accommodative apparatus in primates", Clinical and Experimental Optometry, May 2008, vol. 91, Issue 3, pp. 302-312.

Ehrmann, et al., "Ex Vivo Accommodation Simulator II—Concept and Preliminary Results", Proceedings of SPIE vol. 5314, Ophthalmic Technologies XIV, Jul. 2004, pp. 48-58.

Gabel, et al., "Silicone oil with high specific gravity for intraocular use", British Journal of Ophthalmology, Apr. 1987, vol. 71, 262-267.

Ghallagher-Wetmore, et al., "Supercritical fluid processing: a new dry technique for photoresist developing", SPIE's 1995 Symposium on Microlithography, 1995, vol. 2438, 16 pages.

Kramer, et al., "Prevention of postoperative capsular bag opacification using intraocular lenses and endocapsular devices maintaining an open or expanded capsular bag", Journal of Cataract & Refractive Surgery, Mar. 2016, vol. 42, Issue 3, pp. 469-484.

Lane, et al., "Comparison of the biomechanical behavior of foldable intraocular lenses", Journal of Cataract Refract Surg, Nov. 2004, vol. 30, pp. 2397-2402.

Leishman, et al., "Prevention of capsular bag opacification with a modified hydrophilic acrylic disk-shaped intraocular lens", Journal of Cataract & Refractive Surgery, Sep. 2012, vol. 38, Issue 9, pp. 1664-1670.

Nakamura, et al., "Analysis and Fractionation of Silicone and Fluorosilicone Oils for Intraocular Use", Investigative Ophthalmology & Visual Science, vol. 31, No. 10, Oct. 1990, 2059-2069.

National Center for Biotechnology Information. PubChem Substance Database; SID=184590955, https://pubchem.ncbi.nlm.nih.gov/substance/184590955 (accessed Sep. 20, 2017).

Zhang, et al., "Fluidic adaptive lens with high focal length tunability", Applied Physics Letters, May 2003, vol. 82, No. 19, pp. 3171-3172.

Zhang, et al., "Integrated fluidic adaptive zoom lens", Optics Letters, Dec. 2004, vol. 29, No. 24, pp. 2855-2857.

Zhao, et al., "Strategies for Supercritical $CO_2$ Fractionation of Polydimethylsiloxane," Journal of Applied Polymer Science, 1995, vol. 55, 773-778.

\* cited by examiner

TWO-PART ACCOMMODATING INTRAOCULAR LENS DEVICE

CROSS-REFERENCE TO RELATED APPLICATIONS

This application is a continuation of U.S. Ser. No. 16/207,658, filed Dec. 3, 2018, which is a continuation of U.S. Ser. No. 15/144,544, now U.S. Pat. No. 10,159,564, filed May 2, 2016, which is a continuation of International Patent Application No. PCT/US2014/063538 filed Oct. 31, 2014, which claims the benefit of Provisional Patent Application No. 61/899,110 filed Nov. 1, 2013, both of which are incorporated herein by reference in their entirety.

FIELD OF THE INVENTION

The invention relates generally to an accommodating intraocular lens device and, more particularly, to an accommodating intraocular lens device configured for implantation in a lens capsule of a subject's eye.

BACKGROUND

Surgical procedures on the eye have been on the rise as technological advances permit for sophisticated interventions to address a wide variety of ophthalmic conditions. Patient acceptance has increased over the last twenty years as such procedures have proven to be generally safe and to produce results that significantly improve patient quality of life.

Cataract surgery remains one of the most common surgical procedures, with over 16 million cataract procedures being performed worldwide. It is expected that this number will continue to increase as average life expectancies continue to rise. Cataracts are typically treated by removing the crystalline lens from the eye and implanting an intraocular lens ("IOL") in its place. As conventional IOL devices are primarily focused for distance visions, they fail to correct for presbyopia and reading glasses are still required. Thus, while patients who undergo a standard IOL implantation no longer experience clouding from cataracts, they are unable to accommodate, or change focus from near to far, from far to near, and to distances in between.

Surgeries to correct refractive errors of the eye have also become extremely common, of which LASIK enjoys substantial popularity with over 700,000 procedures being performed per year. Given the high prevalence of refractive errors and the relative safety and effectiveness of this procedure, more and more people are expected to turn to LASIK or other surgical procedures over conventional eyeglasses or contact lens. Despite the success of LASIK in treating myopia, there remains an unmet need for an effective surgical intervention to correct for presbyopia, which cannot be treated by conventional LASIK procedures.

As nearly every cataract patient also suffers from presbyopia, there is convergence of market demands for the treatment of both these conditions. While there is a general acceptance among physicians and patients of having implantable intraocular lens in the treatment of cataracts, similar procedures to correct for presbyopia represent only 5% of the U.S. cataract market. There is therefore a need to address both ophthalmic cataracts and/or presbyopia in the growing aging population.

BRIEF SUMMARY

The two-part accommodating IOL devices disclosed herein provides for a number of advantages owing to its separate two-part construction. Implantation of the IOL device requires a significantly reduced incision size, as the two parts of the IOL device are implanted separately and thus significantly reducing the delivery profile for implantation. The reduced incision size provides for a number of advantages, including obviating the need for anesthesia and sutures to close the incision site and improved surgical outcomes.

Additionally, greater control is afforded with respect to adjusting the sizing and the power of the IOL during surgery. Implanting the primary lens into the lens capsule will provide the physician an impression as to the size of the patient's lens capsule and will thus help verify the correct size of the power changing lens that will subsequently be implanted.

In one embodiment, a two-part accommodating intraocular lens (IOL) device for implantation in a capsular bag of a patient's eye is described. The IOL device comprises a primary lens assembly and a power changing lens assembly. The primary lens assembly comprises a fixed lens and a centration member disposed peripherally of the fixed lens. The centration member has a circumferential distal edge and a first coupling surface adjacent the circumferential distal edge. The power changing lens comprises an enclosed and fluid- or gel-filled lens cavity and a haptic system disposed peripherally of the lens cavity. The haptic system has a peripheral engaging edge configured to contact the capsular bag and a second coupling surface facing the first coupling surface and located adjacent the peripheral engaging edge. The first and second coupling surfaces are in sliding contact with one another to permit movement of the power changing lens relative to the primary lens assembly. The first and second coupling surfaces maintain a spaced relationship between the fixed lens and the lens cavity when the power changing lens is radially compressed.

In accordance with a first aspect, a diameter $d_1$ of the power changing lens is greater than a diameter $d_2$ of the primary lens assembly in the absence of radial compression.

In accordance with a second aspect, the fixed lens does not change shape or curvature during accommodation.

In accordance with a third aspect, the lens cavity changes both shape and curvature during accommodation.

In accordance with a fourth aspect, the fixed lens and the lens cavity are positive power lenses.

In accordance with a fifth aspect, the fluid- or gel-filled lens cavity is a biconvex lens.

In accordance with a sixth aspect, the fixed lens assembly comprises a squared edge located circumferentially around the fixed lens outside of the optical zone.

In accordance with a seventh aspect, the facing surfaces of the centration member and the haptic system each comprise one of a complementary and interlocking pair, the interlocking pair being disposed circumferentially around the fixed lens and the power changing lens, respectively.

In accordance with an eighth aspect, the peripheral engaging edge is thicker than the circumferential distal edge.

In accordance with a ninth aspect, the thickness ratio of the circumferential distal edge to the peripheral engaging edge is in the range of about 1:5 to about 1:2.

In accordance with a tenth aspect, the primary lens assembly has a higher Young's modulus of elasticity than the power changing lens.

In accordance with an eleventh aspect, at least one of the centration member and the haptic system comprises a plurality of openings.

In accordance with a twelfth aspect, the power changing lens is comprised of two opposing surfaces which are displaced away from each other upon the application of a radial force along a peripheral edge, the two opposing surfaces having central and peripheral regions and a gradually increasing thickness profile from the peripheral to the central regions.

In another embodiment, a two-part accommodating intraocular lens (IOL) device for implantation in a capsular bag of a patient's eye is described. The IOL comprises a primary lens assembly and a power changing lens assembly. The primary lens assembly comprises a fixed lens and a centration member disposed peripherally of the fixed lens. The centration member has a radially-compressible peripheral edge having an outer circumferential surface configured to engage the capsular bag of the patient's eye and an inner circumferential surface spaced radially inward of the outer circumferential surface. The power changing lens comprises an enclosed and fluid- or gel-filled lens cavity and a haptic system disposed peripherally of the lens cavity. The haptic system has a circumferential edge configured to engage the inner circumferential surface. Radial compression applied to the outer circumferential surface causes at least one of an increase in curvature and a decrease in diameter of the lens cavity and radial compression applied to the outer circumferential surface does not cause an increase in curvature or a decrease in diameter of the fixed lens.

In accordance with a first aspect, the centration member further comprises circumferential hinges between the fixed lens and the peripheral edge, the circumferential hinges being disposed on opposing sides of the centration member.

In accordance with a second aspect, the centration member further comprises a single circumferential hinge between the fixed lens and the peripheral edge.

In accordance with a third aspect, the circumferential hinge is disposed on an inner surface of the haptic facing the power changing lens.

In accordance with a fourth aspect, the circumferential edge of the haptic system and the inner circumferential surface of the peripheral edge have complementary rounded surfaces and radial compression applied to the outer circumferential surface cause the peripheral edge to tilt radially inwardly about the circumferential hinge.

In accordance with a fifth aspect, the power changing lens is entirely contained within the peripheral edge of the primary lens assembly.

In accordance with a sixth aspect, the power changing lens further comprises a circumferential lip disposed radially inwardly of the inner surface of the circumferential edge.

In accordance with an seventh aspect, the power changing lens is comprised of two opposing surfaces which are displaced away from each other upon the application of a radial force along a peripheral edge, the two opposing surfaces having central and peripheral regions, wherein the region has a thickness that is at least two times, preferably at least three times, and most preferably at least 4 times greater than a thickness of the peripheral region.

In a further embodiment, a method for implanting a two-part IOL device in a capsular bag of a patient's eye is described. The method comprises first inserting and positioning a primary lens assembly in the capsular bag of the patient's eye through an incision located in the cornea, the primary lens having a fixed lens and a centration member disposed peripherally of the fixed lens. The next step comprises inserting and positioning a power changing lens in the capsular bag of the patient's eye anteriorly of the primary lens assembly, the power changing lens comprising an enclosed and fluid- or gel-filled lens cavity and a haptic system disposed peripherally of the lens cavity, the haptic system having a peripheral engaging edge configured to contact the capsular bag. The primary lens assembly is in contact with a posterior portion of the capsular bag and the power changing lens is in contact with the anterior portion of the capsular bag after implantation. The fixed lens and the lens cavity are centered about an optical axis.

In accordance with a first aspect, the incision is less than 5 mm, preferably less than 4 mm, and most preferably less than 3 mm.

In accordance with a second aspect, both of the inserting steps are performed through the incision.

In accordance with a third aspect, the method further comprises injecting a viscoelastic material before the inserting and positioning of the power changing lens.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Illustrative embodiments of the present disclosure are described herein with reference to the accompanying drawings, in which.

Like numerals refer to like parts throughout the several views of the drawings.

DETAILED DESCRIPTION OF THE PREFERRED EMBODIMENTS

Specific, non-limiting embodiments of the present invention will now be described with reference to the drawings.

It should be understood that such embodiments are by way of example and are merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

Figure 1:
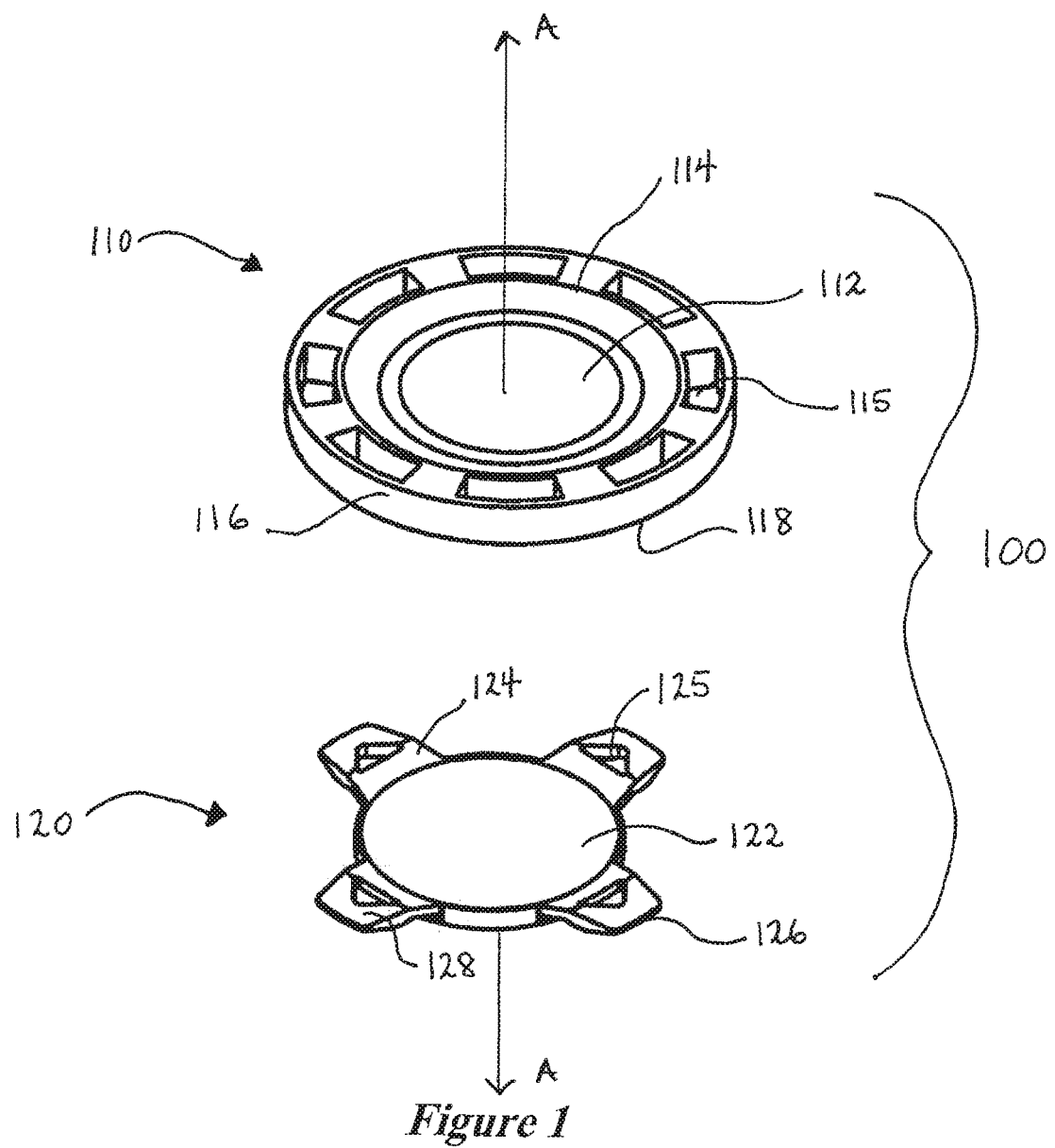
FIG. 1 is an exploded perspective view of an embodiment of the two-part accommodating IOL.
Figure 2:
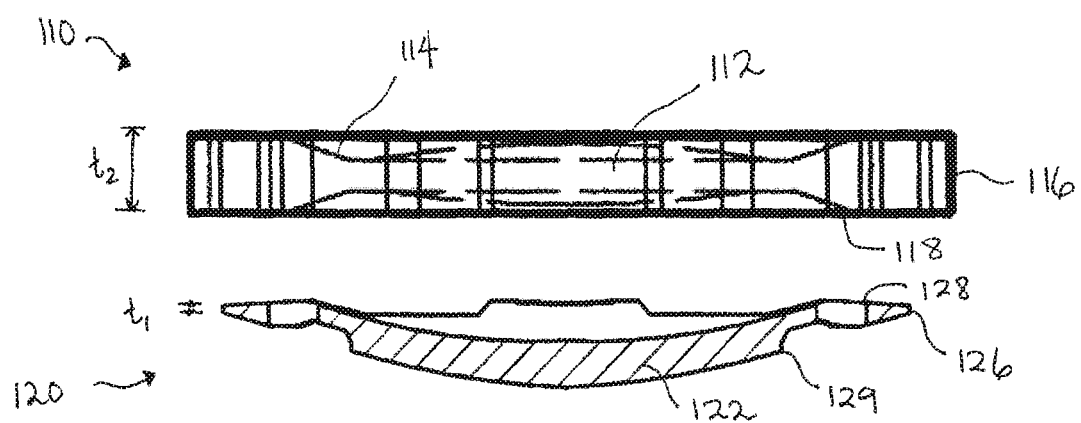
FIG. 2 is an exploded side cross-sectional view of the two-part accommodating IOL of FIG. 1.
Figure 3:
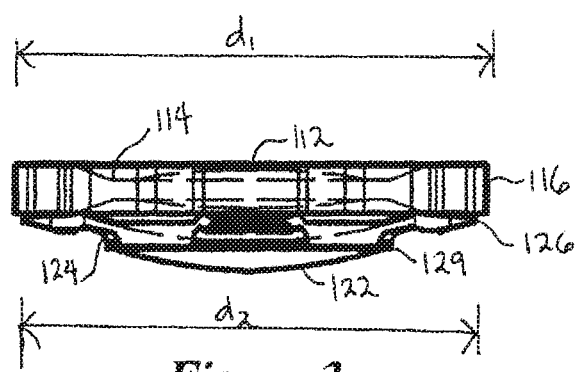
FIG. 3 is an assembled side view of the two-part accommodating IOL of FIG. 1, in which the power changing lens and the primary lens are in sliding contact with one another.

FIGS. 1-3 depict an embodiment of a two-part accommodating IOL device 100 in which the power changing lens 110 and the primary lens 120 are in sliding contact with one another.

The power changing lens 110 is depicted as comprising a fluid- or gel-filled lens chamber 112 and a haptic system 114 disposed peripherally of the fluid- or gel-filled lens chamber 112. The haptic system 114 comprises a peripheral engaging edge 116 that is configured to engage the capsular bag of the patient's eye, generally at a location where it is attached via zonules to the ciliary muscles. A plurality of through holes 115 may be disposed along the circumference of the haptic system 114 to reduce material bulk and thus the delivery profile of the power changing lens 110.

The primary lens 120 is depicted as comprising a fixed-power lens 122 and a plurality of centration members 124 disposed symmetrically about the fixed-power lens. The centration member 124 comprises a distal edge 126 and through holes 125 to reduce the resistance to radial compression exerted by the capsular bag.

The presence of the holes 115 in the power lens 110 allows the manipulation of both the power lens 110 and the primary lens 120 underneath it. The holes 115 also help reduce the delivery profile of the power lens 110 and permits both the power lens 110 and the primary lens 120 to be manipulated to center it in the capsular bag during implantation. The presence of holes 115 may also reduce the rigidity of the power lens. Similarly, the primary lens 120 also has holes 125 that permit manipulation and reduce delivery profile. The holes 125 of the primary lens 120 are additionally shaped so as to reduce the likelihood of grabbing the power changing lens 110 when the power changing lens 110 is implanted into the capsular bag of the patient's eye after the primary lens 120 has already been implanted.

The power changing lens 110 and the primary lens 120 is configured to be in sliding contact with one another, while maintaining a separation between the fluid- or gel-filled lens chamber 112 and the fixed-power lens 122. In one embodiment, this distance is maintained by angling either one or both of the haptic system 114 and the centration member 124 towards one another. As shown in FIGS. 2 and 3, the sliding contact between the power changing lens 110 and the primary lens 120 is made at the first and second coupling surfaces 118, 128, respectively.

The power changing lens 110 is sized and shaped to take on and respond to the radially-inward forces which are applied along the peripheral edge 116 of the lens 110. In contrast, the primary lens 120 does not participate in providing an accommodative response and thus is sized and shaped so as to avoid interfering or resisting the radial compressive forces that are applied to the power changing lens 110. This may be accomplished by controlling the relative diameters and thicknesses of the power changing lens 110 and the primary lens 120 to maximize the extent to which the radial compressive forces are applied onto the power changing lens 110 and to minimize the extent to which these forces are applied onto the primary lens 120.

In a preferred embodiment, as depicted in FIG. 2, the thickness $t_1$ of peripheral engaging edge 116 of the power changing lens 110 is substantially thicker than the thickness $t_2$ of the distal edge 126 of the fixed-power lens 122. In a preferred embodiment, the thickness ratio of $t_1$ to $t_2$ is 2:1, preferably 3:1, more preferably 4:1 and most preferably 5:1. In another preferred embodiment, as depicted in FIG. 3, the diameter $d_1$ of the power changing lens 110 is greater than the diameter $d_2$ of the primary lens 120.

In one preferred embodiment, at least the opposing sides or walls of the lens chamber 112 is made of a material of sufficient mechanical strength to withstand physical manipulation during implantation, but is of sufficiently low Young's modulus so as to minimize its resistance to deformation. In a preferred embodiment, the opposing sides of the lens chamber 112 is made of a polymer having a Young's modulus of 100 psi or less, preferably 75 psi or less, and most preferably 50 psi or less. In one preferred embodiment, the remaining portions of the IOL 100 has a Young's modulus that is greater than the Young's modulus of the lens chamber 112. The walls of the lens chamber 112 may be a polymer, preferably a silicone polymer and more preferably a phenyl siloxane, such as a vinyl-terminated phenyl siloxane or a vinyl-terminated diphenyl siloxane. In order to impart sufficient mechanical strength, the polymer may be crosslinked, reinforced with fillers, or both. The fillers may be a resin or silica that have been functionalized to react with the polymer.

The walls of the lens chamber 112 define an enclosed cavity that is filled with a fluid or gel having specific physical and chemical characteristics to enhance the range of refractive power provided by the IOL during accommodation. The fluid or gel is selected such that it cooperates with the power changing lens 110 in providing a sufficient range of accommodation of up to at least 3 diopters, preferably up to at least 5 diopters, preferably up to at least 10 diopters and most preferably up to at least 15 diopters. In a preferred embodiment, the enclosed cavity is filled with the fluid or gel before implantation of the IOL 100 into the capsular bag 40 of the eye and, in a more preferred embodiment, the cavity is filled with the fluid or gel in the manufacture of the IOL 100.

FIGS. 4A-4F and 8-10 more clearly depict the location of the fluid or gel (213, 313, 413, 513) contained within the power changing lens (210, 310, 410, 510). In one preferred embodiment the enclosed cavity defined by the walls of the lens chamber 112 is filled with a fluid, such as a gas or a liquid, having low viscosity at room temperature and a high refractive index. In a preferred embodiment, the fluid (213, 313, 413, 513) is a liquid having a viscosity of 1,000 cP or less at 23° C. and a refractive index of at least 1.46, 1.47, 1.48, or 1.49. The fluid may be a polymer, preferably a silicone polymer, and more preferably a phenyl siloxane polymer, such as a vinyl-terminated phenyl siloxane polymer or a vinyl-terminated diphenyl siloxane polymer. Preferably in embodiments where the fluid is made of a polymer, the polymer is preferably not crosslinked and the polymer may be linear or branched. Where the fluid is a vinyl-terminated phenyl siloxane polymer or diphenyl siloxane polymer, the vinyl groups may be reacted to form other moieties that do not form crosslinkages.

In accordance with one embodiment, fluid (213, 313, 413, 513) may be a polyphenyl ether ("PPE"), as described in U.S. Pat. No. 7,256,943, entitled "Variable Focus Liquid-Filled Lens Using Polyphenyl Ethers" to Teledyne Licensing, LLC, the entire contents of which are incorporated herein by reference as if set forth fully herein.

In accordance with another embodiment, the fluid (213, 313, 413, 513) may be a fluorinated polyphenyl ether ("FPPE"). FPPE has the unique advantage of providing tunability of the refractive index while being a chemically inert, biocompatible fluid with dispersion properties. The tunability is provided by the increasing or decreasing the phenyl and fluoro content of the polymer. Increasing the phenyl content will effectively increase the refractive index of the FPPE, whereas increasing the fluoro content will decrease the refractive index of the FPPE while decreasing the permeability of the FPPE fluid through the walls of the lens chamber 112.

In another preferred embodiment, the enclosed cavity defined by walls of the lens chamber 112 is filled with a gel (213, 313, 413, 513). The gel (213, 313, 413, 513) preferably has a refractive index of at least 1.46, 1.47, 1.48, or 1.49. The gel may also preferably have a Young's modulus of 20 psi or less, 10 psi or less, 4 psi or less, 1 psi or less, 0.5 psi or less, 0.25 psi or less and 0.01 psi or less. In a preferred embodiment, the gel (213, 313, 413, 513) is a crosslinked polymer, preferably a crosslinked silicone polymer, and more preferably a crosslinked phenyl siloxane polymer, such as a vinyl-terminated phenyl siloxane polymer or a vinyl-terminated diphenyl siloxane polymer. Other optically clear polymer liquids or gels, in addition to siloxane polymers, may be used to fill the enclosed cavity and such polymers may be branched, unbranched, crosslinked or uncrosslinked or any combination of the foregoing.

A gel has the advantages of being extended in molecular weight from being crosslinked, more self-adherent and also adherent to the walls or opposing sides lens chamber 112 than most liquids. This makes a gel less likely to leak through the walls of the power changing lens. In order to obtain the combination of accommodative power with relatively small deformations in the curvature of the power changing lens, the gel (213, 313, 413, 513) is selected so as to have a high refractive index while being made of an optically clear material that is characterized as having a low Young's modulus. Thus, in a preferred embodiment, the gel has a refractive index of 1.46 or greater, preferably 1.47 or greater, 1.48 or greater and most preferably 1.49 or greater. At the same time, the gel preferably has a Young's modulus of 10 psi or less, preferably 5 psi or less, and more preferably 1 psi or less. In a particularly preferred embodiment, the gel has a Young's modulus of 0.5 psi or less, preferably 0.25 psi or less, and most preferably 0.01 psi or less. It is understood that at lower Young's modulus, the gel will present less resistance to deformation and thus the greater the deformation of the power changing lens 110 for a given unit of applied force.

In particularly preferred embodiment, the gel is a vinyl-terminated phenyl siloxane that is produced based on one of the four formulas provided as follows:

Formula 1:
100 parts 20-25 mole % vinyl terminated diphenylsiloxane-dimethylsiloxane copolymer (Gelest PDV 2335).
3 ppm platinum complex catalyst
0.35 pph of phenyl siloxane hydride crosslinker (Nusil XL-106)
Young's modulus of elasticity=0.0033 psi Formula 2:
100 parts 20-25 mole % vinyl terminated diphenylsiloxane-dimethylsiloxane copolymer (Gelest PDV 2335).
3 ppm platinum complex catalyst
0.4 pph of phenyl siloxane hydride crosslinker (Nusil XL-106)
Young's modulus of elasticity=0.0086 psi Formula 3:
100 parts 20-25 mole % vinyl terminated diphenylsiloxane-dimethylsiloxane copolymer (Gelest PDV 2335).
3 ppm platinum complex catalyst
0.5 pph of phenyl siloxane hydride crosslinker (Nusil XL-106)
Young's modulus of elasticity=0.0840 psi Formula 4:
100 parts 20-25 mole % vinyl terminated diphenylsiloxane-dimethylsiloxane copolymer (Gelest PDV 2335).
3 ppm platinum complex catalyst
0.6 pph of phenyl siloxane hydride crosslinker (Nusil XL-106)
Young's modulus of elasticity=2.6 psi The walls of the lens chamber and the fluid or gel contained within the cavity is preferably selected so as to prevent or reduce the likelihood of the fluid or gel migrating outside of the lens chamber. Thus, in a preferred embodiment, one or both of the power changing lens and the fluid or gel (213, 313, 413, 513) is/are selected from biocompatible materials that optimize the resistance to permeability of the fluid or gel across the power changing lens.

One method of decreasing the permeability of the gel contained inside the cavity and across the power changing lens is to provide a gel that is cross-linked. The degree of cross-linking, however, must be selected and controlled such that, on the one hand, the power changing lens and the gel have a sufficiently low Young's modulus to minimize the resistance of the power changing lens to deformation and, on the other hand, to minimize the permeation of the gel across the power changing lens. Thus, in a preferred embodiment, longer chain polymers that are lightly cross-linked, such as those used for silicone gels, starting with monomers having molecular weights that are greater than 35,000 daltons, preferably greater than 50,000 daltons and, most preferably, at least 70,000 daltons are desired.

In another preferred embodiment, a gel is used having low permeability extractables. Such gels may be formulated by using long chain polymers that are branched.

In a preferred embodiment, one or both of the lens chamber walls and the gel may be made of homo- or co-polymers of phenyl-substituted silicones.

For the lens chamber walls, the crosslinked homo- or co-polymers preferably have a diphenyl content of 5-25 mol %, preferably 10-20 mol % and more preferably 15-18 mol %. Alternatively, for the lens chamber walls, the homo- or co-polymers preferably have a phenyl content of 10-50 mol %, preferably 20-40 mol %, and more preferably 30-36 mol %.

For the gel, the homo- or co-polymers preferably have a diphenyl content of 10-35 mol %, preferably 15-30 mol % and more preferably 20-25 mol %. Alternatively, for the gel, the homo- or co-polymers preferably have a phenyl content of 20-70 mol %, preferably 30-60 mol % and more preferably 40-50 mol %.

In a particularly preferred embodiment, the walls of the lens chamber are made of a crosslinked phenyl siloxane having a diphenyl content of about 15-18 mol % or a phenyl content of about 30-36 mol % and the gel is made of a phenyl siloxane having a diphenyl content of about 20-25 mol % or a phenyl content of about 40-50 mol %. The walls of the lens chamber walls are understood to be more crosslinked than the gel.

In a particularly preferred embodiment, the lens chamber walls are made of a vinyl-terminated phenyl siloxane, most preferably a crosslinked vinyl-terminated phenyl siloxane.

Reinforcing agents, such as silica, may also be included in a range of 10-70 mol %, preferably 20-60 mol % and most preferably 30-50 mol %.

The walls of the lens chamber and the fluid or gel contained within the cavity is also preferably selected so as to increase the range of accommodative power that is provided by the lens chamber. In one preferred embodiment, the walls of the lens chamber are made of a material having a lower refractive index than the fluid or gel contained in the enclosed cavity. In one preferred embodiment, the refractive index of the walls of the lens chamber is 1.38 and the refractive index of the gel or fluid contained therein is 1.49.

The differential refractive indices provided by the lens chamber walls and the gel or liquid contained within the lens chamber may be provided by differences in the materials or the composition of the materials used for the lens chamber walls and the gel or liquid.

In one embodiment, both the lens chamber walls and the gel or liquid is made of a phenyl siloxane having different diphenyl or phenyl content. In a preferred embodiment, the lens chamber walls have a diphenyl or phenyl content that is less than that for the gel or liquid. In another preferred embodiment, the walls of the lens chamber may be made of a cross-linked vinyl-terminated phenyl siloxane having a diphenyl content of about 15-18 mol % or a phenyl content of about 30-36 mol % and the gel contained within the lens chamber walls may be made of a vinyl-terminated phenylsiloxane having a diphenyl content of 20-25 mol % or a phenyl content of 30-36 mol %.

In another embodiment, the differential refractive indices may be provided by providing a dimethyl siloxane for the lens chamber walls and the gel may be a phenyl siloxane having a high diphenyl or phenyl content. In a preferred embodiment, the diphenyl content is at last 20 mol %, at least 25 mol %, at least 30 mol %, at least 35 mol %, and at least 40 mol %. Alternatively, the phenyl content is at least 40 mol %, at least 50 mol %, at least 60 mol %, at least 70 mol % and at least 80 mol %.

In a further embodiment, the differential refractive indices may be provided by a crosslinked fluoro siloxane, such as a 3,3,3-trifluoropropylmethyl siloxane and the gel may be a phenyl siloxane having a high diphenyl or phenyl content. In a preferred embodiment, the diphenyl content is at least 20 mol %, at least 25 mol %, at least 30 mol %, at least 35 mol %, and at least 40 mol %. Alternatively, the phenyl content is at least 40 mol %, at least 50 mol %, at least 60 mol %, at least 70 mol %, and at least 80 mol %.

FIGS. 4A-4F depict alternate embodiments of the two-part IOL device 200A-F in which the shape and configuration of the power changing lens 210 and the primary lens 230 are varied.

In each of these embodiments, certain features remain the same. The power changing lens 210 is depicted as comprising a fluid- or gel-filled lens chamber 212 and a haptic system 214 disposed peripherally of the fluid- or gel-filled lens chamber 212. The lens chamber 212 comprises two opposing surfaces which are divided into a central regions 212a, 212b about the central axis A-A (See FIG. 1) and peripheral regions 211a, 211b. In a preferred embodiment, the central regions 212a, 212b have a gradually increasing thickness radially towards the center of the lens chamber 212 from the peripheral regions 211a, 211b.

In a preferred embodiment, the center point of the central regions 212a, 212b has a thickness that is two times or more, preferably three times or more, and most preferably 4 times or more than the thickness of the peripheral region 211a, 211b. A fluid or gel 213 is contained between the opposing surfaces. In another preferred embodiment, the point of greatest thickness in the central region 212a, 212b and the point of least thickness in the peripheral region 211a, 211b is a ratio of 2:1 or greater, preferably 3:1 or greater, and most preferably 4:1 or greater. In a preferred embodiment, the thickness at the optical axis or the center of the central region 212a, 212b is about 200 microns and the thickness at the peripheral region 211a, 211b is about 50 microns. The increased thickness in the central region 212a, 212b is provided so as to prevent the opposing surfaces of the lens chamber 212 from buckling when it is deformed in response to accommodation. It is understood that in the various embodiments of the power lens depicted in the figures, the opposing sides preferably has the thickness profiles as described herein and depicted in FIGS. 4A-4F. References to the optical axis or optical axis A-A made herein is understood to mean the line bisecting the center of the IOL device, as shown in FIG. 1.

The opposing surfaces of the lens chamber 212 actuate towards and away from each other when the eye is unaccommodated and accommodated, respectively. The haptic system 214 comprises a peripheral engaging edge 216 and a first coupling surface 218 adjacent the peripheral engaging edge 216. The primary lens assembly 230 comprises a fixed lens 232 and a plurality of centration members 224 disposed about the fixed lens 232. The centration members 224 comprise a distal edge 236 and a second contacting surfaces 238 in sliding contact with the first contacting surfaces 218 of the power changing lens 210.

In a preferred embodiment, the primary lens 230 is substantially thicker than one of the opposing sides lens chamber 212, as measured along the optical axis A-A. In a preferred embodiment, the thickness of each one of the opposing sides lens chamber 212, as along the optical axis A-A is less than ½, preferably less than ⅓, preferably less than ¼, and most preferably less than ⅕ of the thickness of the primary lens 230 at the central optical axis A-A. Because the primary lens 230 is substantially thicker than either one of the opposing sides lens chamber 212, the primary lens 230 has an effective Young's modulus that is substantially greater than either one of the opposing sides of the chamber 212.

Figure 4A:
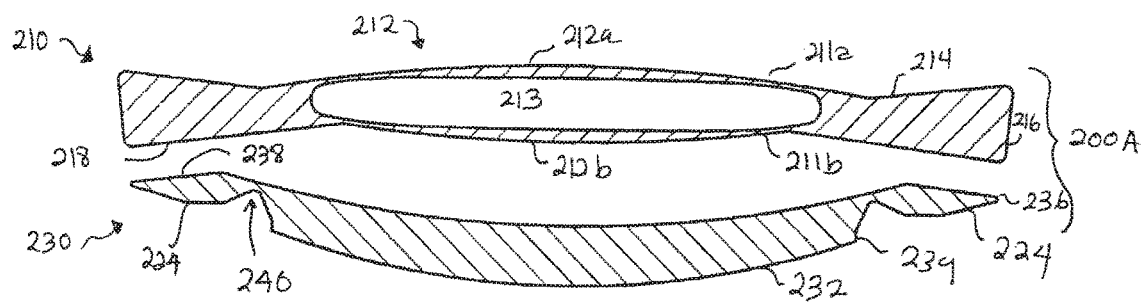
FIG. 4A through 4F are a cross-sectional view of various embodiments of the two-part accommodating IOL.

Turning now to the various distinguishing features of the two-part IOL devices, reference is made with respect to FIG. 4A of the IOL device 200A in which the primary lens 230 is depicted as comprising a hinge 240 and angled or squared edge 239. The hinge 240 is provided on the centration members 224 to permit it to bend axially, compress radially, or both in response the accommodative forces exerted on the capsular bag. The hinge 240 therefore permits these accommodative forces to act upon the peripheral engaging edge 216 of the power changing lens 210 to actuate the opposing surfaces 212a, 212b away from or towards one another. The squared edge 239 is provided to help fix the primary lens assembly to the capsular bag and also to reduce the likelihood of posterior capsular opacification (PCO) from occurring.

Figure 4B:
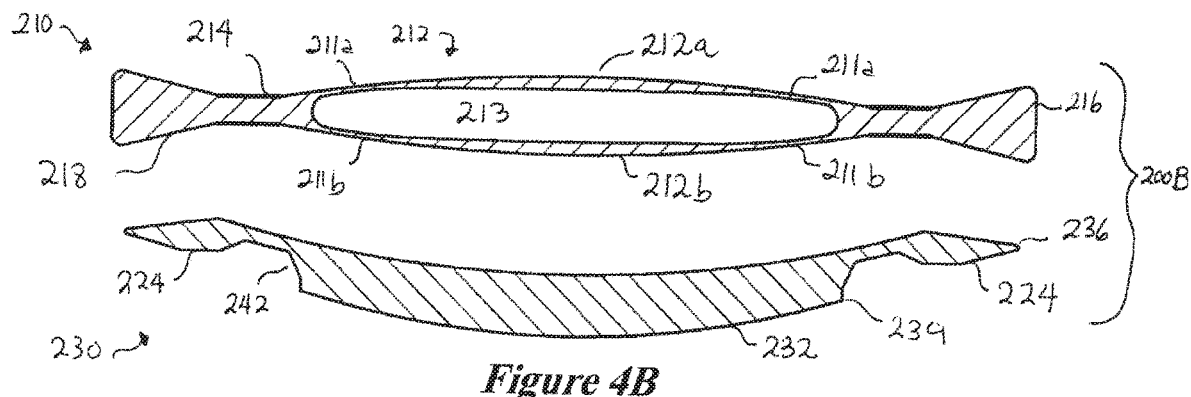

FIG. 4B depicts an IOL device 200B that is similar in many respects with FIG. 4A with the exception that the hinge 242 disposed on the centration members 224 is substantially wider so as to provide less resistance to bending, compression or both in response to the accommodative forces exerted on the capsular bag and thus onto the distal edge 236 of the centration member 224. It is understood that for both IOL devices 200A, 200B, the hinge 240 is provided on the surface facing away from the power changing lens 210 and therefore the distal edge 236 pivot in a direction away from the power changing lens 210 when a radially compressive force is applied to the distal edge 236.

Figure 4C:
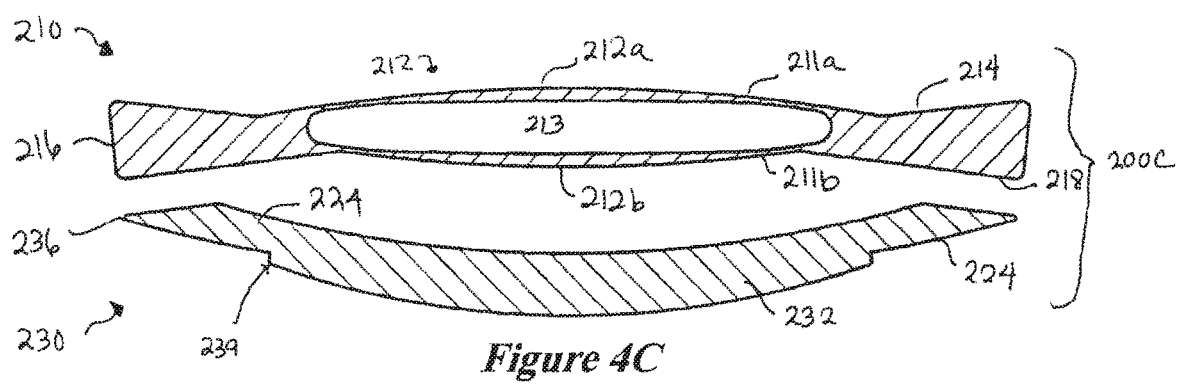

FIG. 4C depicts an IOL device 200C in which the primary lens assembly 230 comprises only a squared edge 239 around the periphery of the fixed lens 232. Because the primary lens assembly 230 does not include a hinge, it is expected that this IOL device 200C will be significantly more rigid than the IOL devices 200A and 200B depicted in FIGS. 4A and 4B, respectively.

Figure 4D:
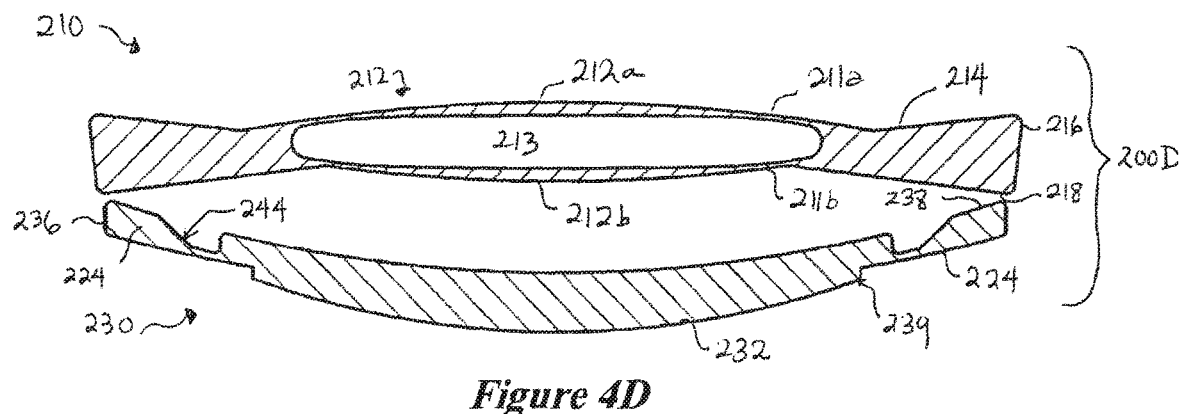

FIG. 4D depicts an IOL device 200D in which is similar to the IOL device 200B of FIG. 4B with the exception that the hinge 244 is now located on the surface facing the power changing lens 210. Thus, the distal edge 236 will pivot in a direction toward the power changing lens 210 when a radially compressive force is applied to the distal edge 236.

Figure 4E:
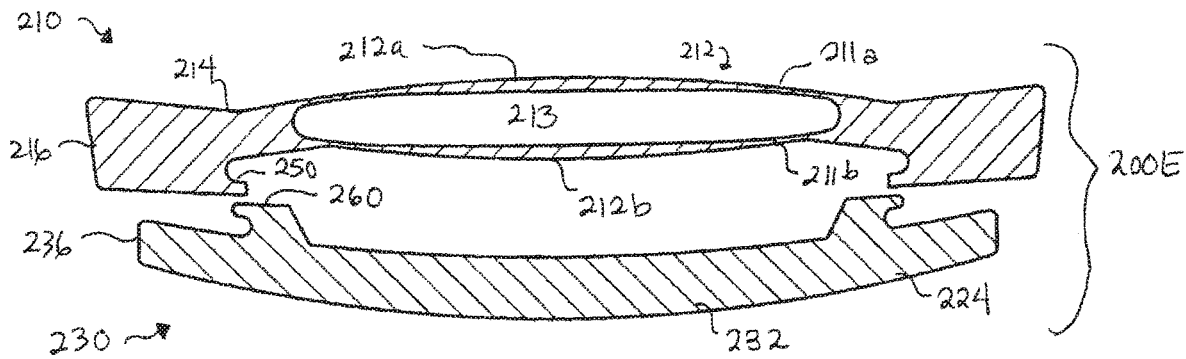

FIG. 4E depicts an IOL device 200E having a greater degree of engagement between the power changing lens 210 and the fixed lens assembly 230. The power changing lens 210 and the fixed lens assembly 230 comprise complementary and interlocking hooks 250, 260 disposed peripherally of the fluid- or gel-filled lens chamber 212 and the fixed lens 232, respectively. Unlike the IOL devices depicted in FIGS. 4A-4D, the power changing lens 210 and the fixed lens assembly 230 are coupled to one another by engagement of the interlocking hooks 250, 260.

Figure 4F:
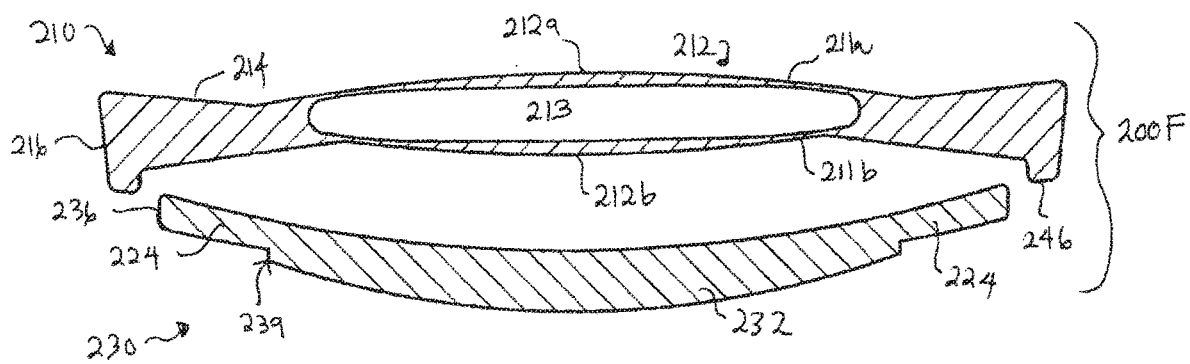

FIG. 4F depicts an IOL device 200F in which the power changing lens 210 comprises a circumferential projection 246 downwardly of the peripheral engaging edge 216 to constrain the movement of the fixed lens assembly 230 within the boundary defined by the circumferential portion 246. As a result, it is understood that the fixed lens assembly 230 has a diameter that is less than the diameter defined by the circumferential projection 246.

Figure 5:
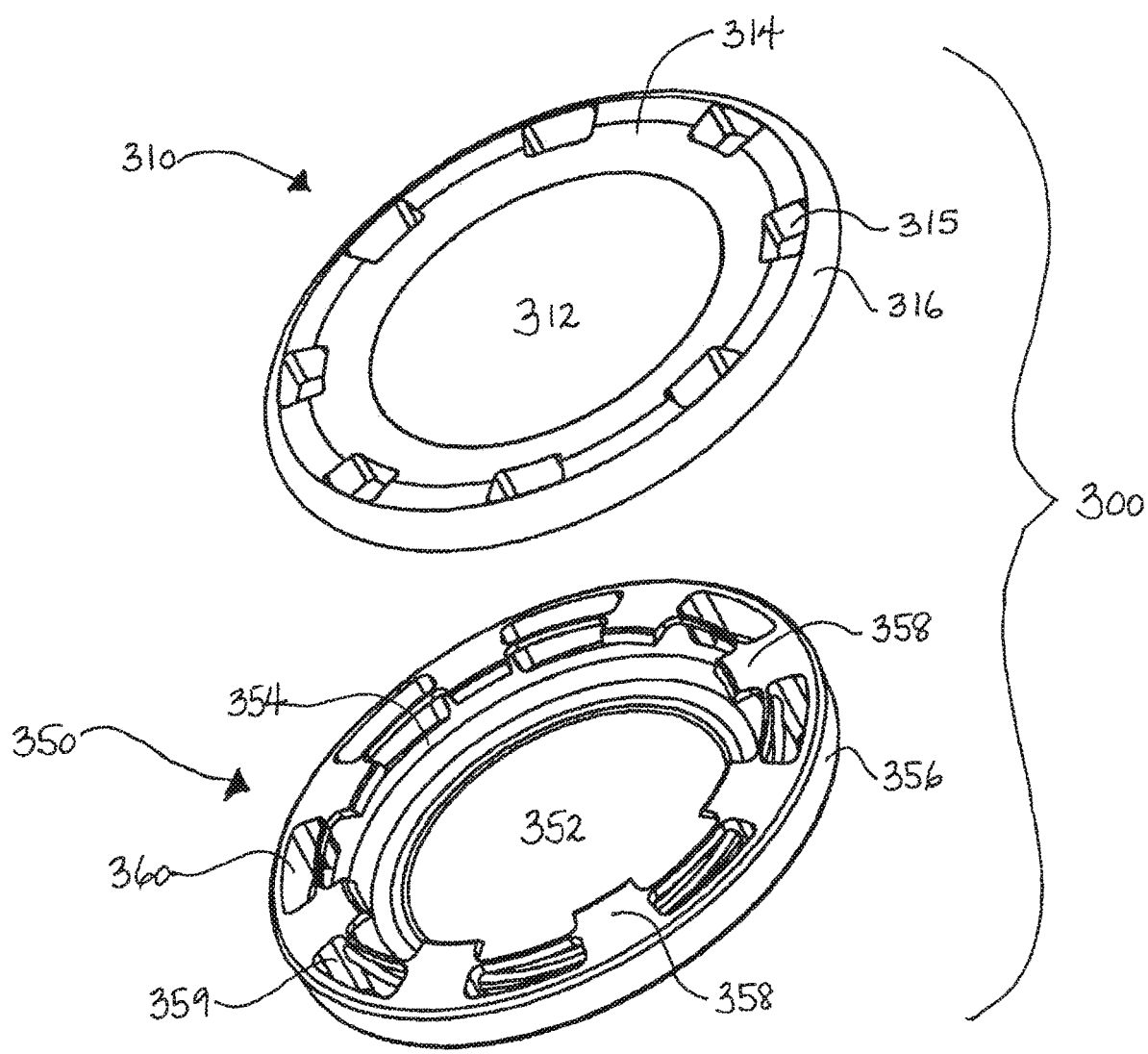
FIG. 5 is an exploded perspective view of an embodiment of the two-part accommodating IOL.
Figure 6A:
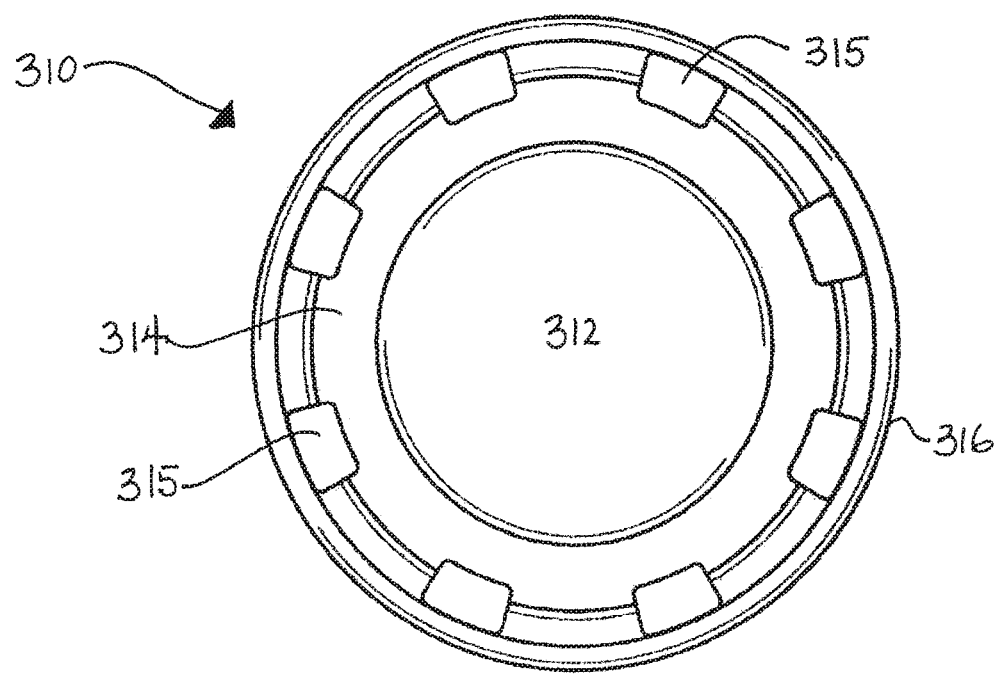
FIGS. 6A and 6B are a top and side plan views of the power-changing lens of the two-part IOL of FIG. 5.
Figure 6B:
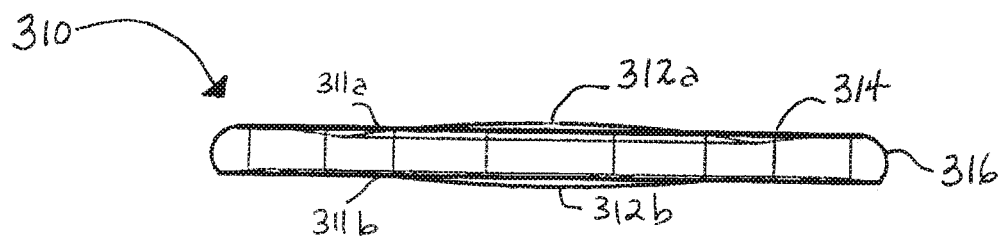
Figure 7A:
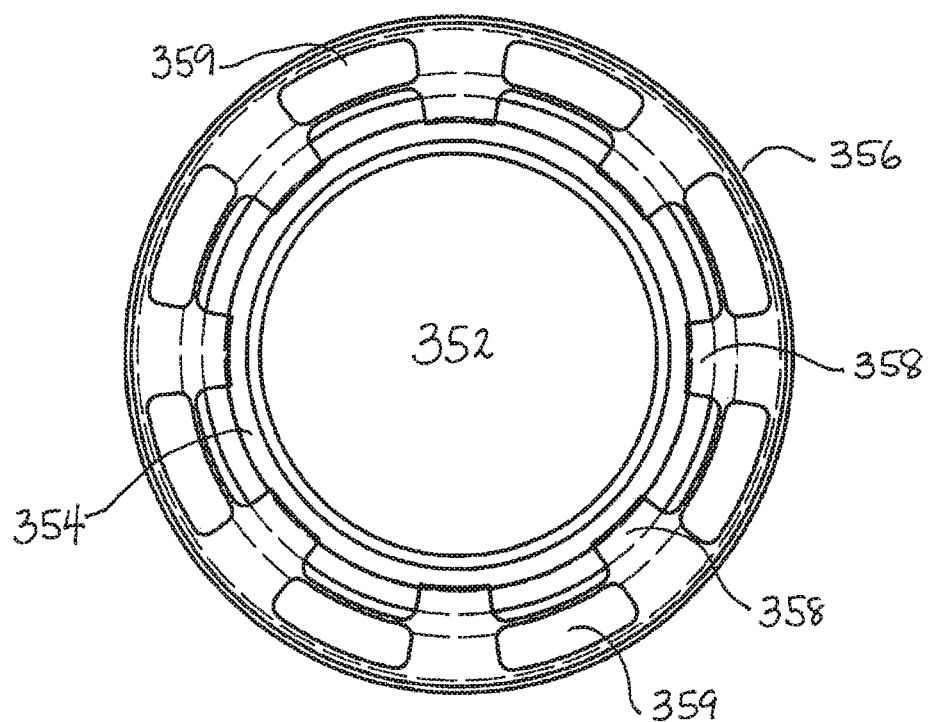
FIGS. 7A and 7B are top and side plan views of the primary lens of the two-part IOL of FIG. 5.
Figure 7B:
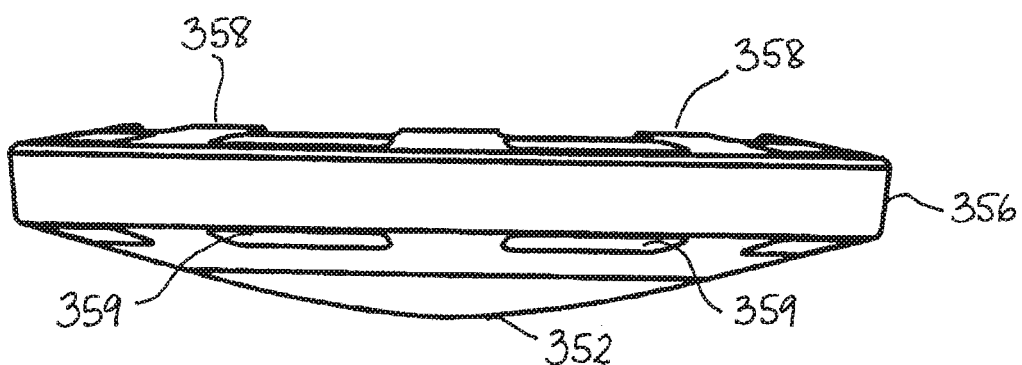

FIGS. 5-8 depict another embodiment of a two-part IOL device 300 in which the power changing lens 310 is constrained within the boundaries of the fixed lens assembly 350. As shown in FIGS. 5-6, the power changing lens 310 has a roughly disc-shaped outer surface and comprises an enclosed fluid- or gel-filled lens 312, a haptic system 314 and a circumferential peripheral engaging edge 316. The power changing lens 310 further comprises a plurality of circumferential holes 315 disposed peripherally of the enclosed fluid- or gel-filled lens 312. The fluid- or gel-filled lens 312 comprises two opposing surfaces which are divided into central regions 312a, 312b and peripheral regions 311a, 311b. In a preferred embodiment, the central regions 312a, 312b have a gradually increasing thickness radially towards the center of the fluid- or gel-filled lens 312 from the peripheral regions 311a, 311b. In a preferred embodiment, the center point of the central regions 312a, 312b has a thickness that is two times or more, preferably three times or more, and most preferably 4 times or more than the thickness of the peripheral region 311a, 311b. A fluid or gel 313 is contained between the opposing surfaces. In another preferred embodiment, the point of greatest thickness in the central region 312a, 312b and the point of least thickness in the peripheral region 311a, 311b is a ratio of 2:1 or greater, preferably 3:1 or greater, and most preferably 4:1 or greater. In a preferred embodiment, the thickness at the optical axis or the center of the central region 312a, 312b is about 200 microns and the thickness at the peripheral region 311a, 311b is about 50 microns. The increased thickness in the central region 312a, 312b is provided so as to prevent the opposing surfaces of the fluid- or gel-filled lens 312 from buckling when it is deformed in response to accommodation.

Figure 8A:
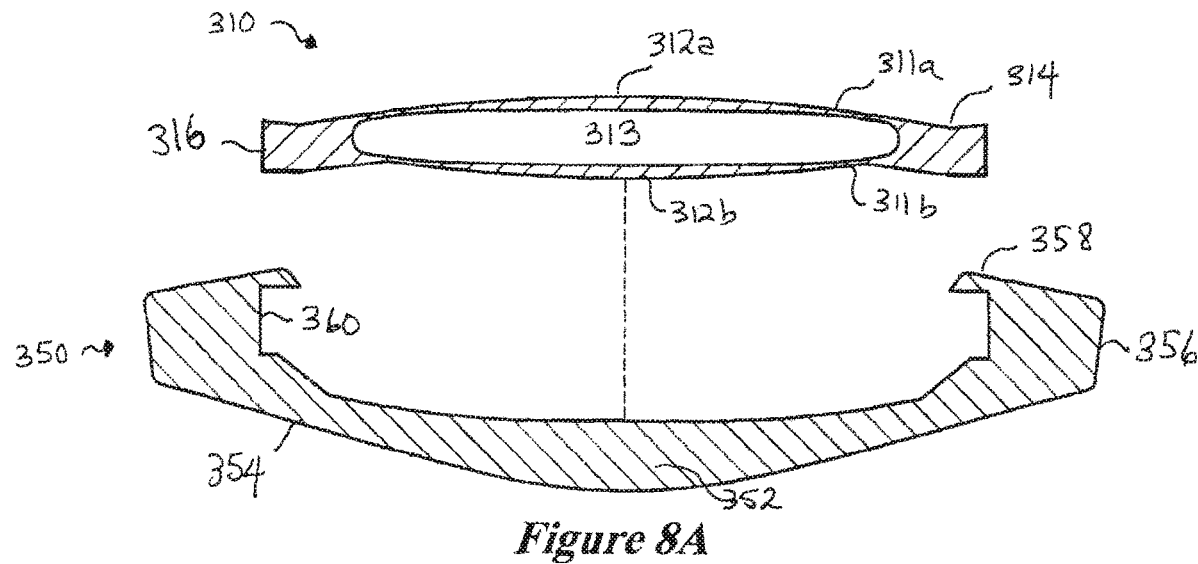
FIGS. 8A and 8B are exploded and coupled cross-sectional views of another embodiment of a two-part accommodating IOL in which the power changing lens and the primary lens are coupled together.
Figure 8B:
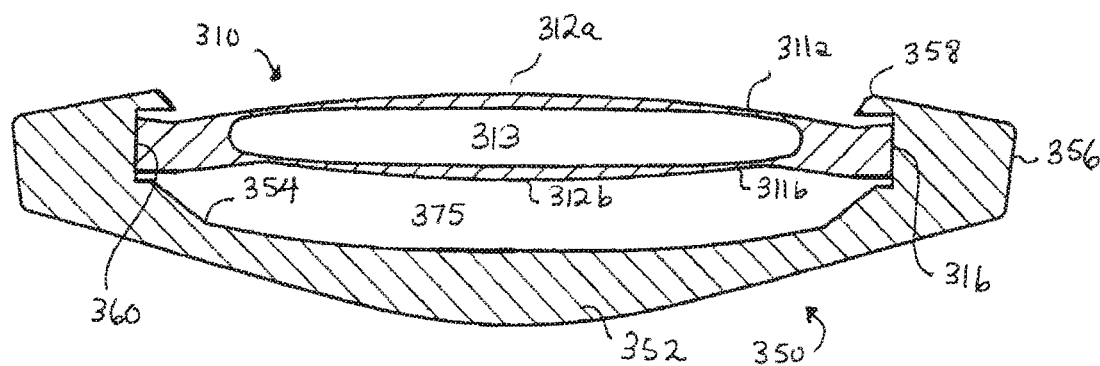

The fixed lens assembly 350 is configured to house and receive the power changing lens 310. The fixed lens assembly 350 comprises a fixed lens 352 centrally disposed and an internal cavity defined by the fixed lens 352, the peripheral side wall 356 and a plurality of radial protrusions 358 projecting inwardly from the top of the peripheral side wall 356. Circumferential grooves or hinges 354 surround the fixed lens 352 and permit pivoting or compression of the peripheral side wall 356 radially inward. A plurality of circumferential holes 359 are provided about the periphery of the fixed lens 352 to permit the flow of aqueous fluid therethrough and into the cavity 375 (FIG. 8B) defined between the power changing lens 310 and the fixed lens assembly 350. The holes 359 also to reduce the material bulk and thus the delivery profile of the fixed lens assembly 350. As shown in FIG. 8B, a space 375 is defined between the power changing lens 310 and the fixed lens assembly 350.

The implantation and assembly of the two-part IOL device 300 follows two steps. In a first step, the fixed lens assembly 350 is inserted into the capsular bag of the eye following capsulhorexis. The fixed lens assembly 350 is centered such that the peripheral side wall 356 engages the circumferential area of the capsular bag that is most densely connected to the zonules and the fixed lens 352 is centered about the optical axis and is in contact with the posterior portion of the capsular bag. In a second step, the power changing lens 310 is inserted into the capsular bag and positioned within the cavity 375 of the fixed lens assembly 350 such that the peripheral engaging edge 316 is in proximity to or in contact with the inner surface 360 of the peripheral side wall 356. Thus, radial compression applied to the peripheral side wall 356 is transmitted to the peripheral engaging edge 316 of the power changing lens 310 such that the fluid- or gel-filled lens increases and decreases in curvature to provide an accommodating response to the relaxation and contraction of the ciliary muscles of the eye, respectively.

FIGS. 9-10 are cross-sectional views of various embodiments of the two-part IOL device.

Figure 9A:
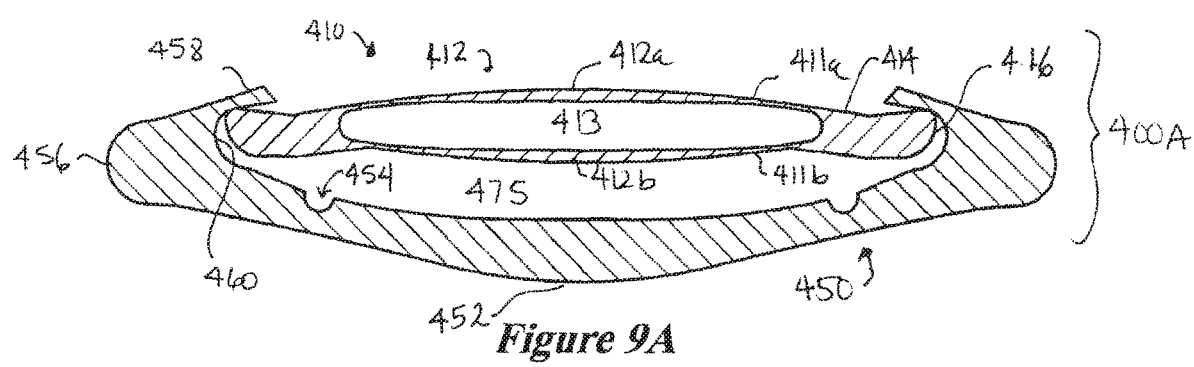
FIGS. 9A and 9B are cross-sectional views of alternate embodiments of a two-part accommodating IOL in which the power changing lens and the primary lens are coupled together.
Figure 9B:
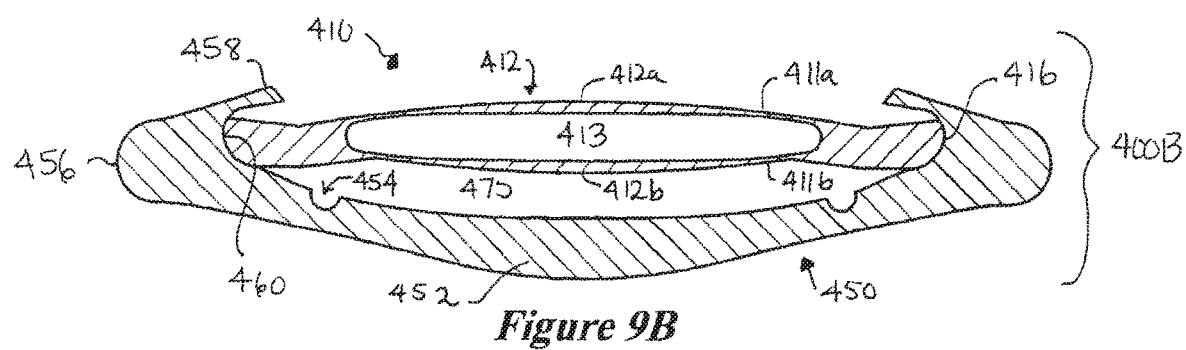

FIGS. 9A and 9B are cross-sectional view of two alternate embodiments of the two-part IOL device 400A, 400B. In both embodiments, the two-part IOL device comprises a power changing lens 410 and a fixed lens assembly 450. The power changing lens 410 comprises a fluid- or gel-filled lens chamber 412 defined by opposing surfaces and a fluid or gel 413 contained therein. A haptic 414 having an engaging edge 416 is provided peripherally of the lens chamber 412. The fixed lens assembly 450 comprises a centrally-disposed fixed lens 452 and a hinge 454 disposed peripherally of the lens 452. The hinge 454 is preferably disposed on the surface of the fixed-lens assembly 450 facing the power changing lens 410 such that radial compressive forces applied to the circumferential periphery 456 causes it to pivot towards the power changing lens 410 and thus transmit the radially-compressive forces onto the engaging edge 416 of the fluid- or gel-filled lens 412 to effectuate a curvature change in the opposing sides of the fluid- or gel-filled lens chamber 412. The difference between the IOL devices 400A and 400B is that the engaging edge 416 in 400A is in spaced relation to the inner surface 460 of the circumferential periphery 456, whereas the engaging edge 416 in 400B is in contact with the inner surface 460 of the circumferential periphery 456 in the absence of a radially-applied force.

Additionally the IOL devices 400A, 400B are provided with curved surfaces at the points of contact between the power changing lens 410 and the fixed lens assembly 450 to facilitate a sliding movement between them. Thus, in a preferred embodiment, at least the circumferential periphery 456, the engaging edge 416 and the inner surface 460 of the circumferential periphery 456 are curved surfaces.

Figure 10A:
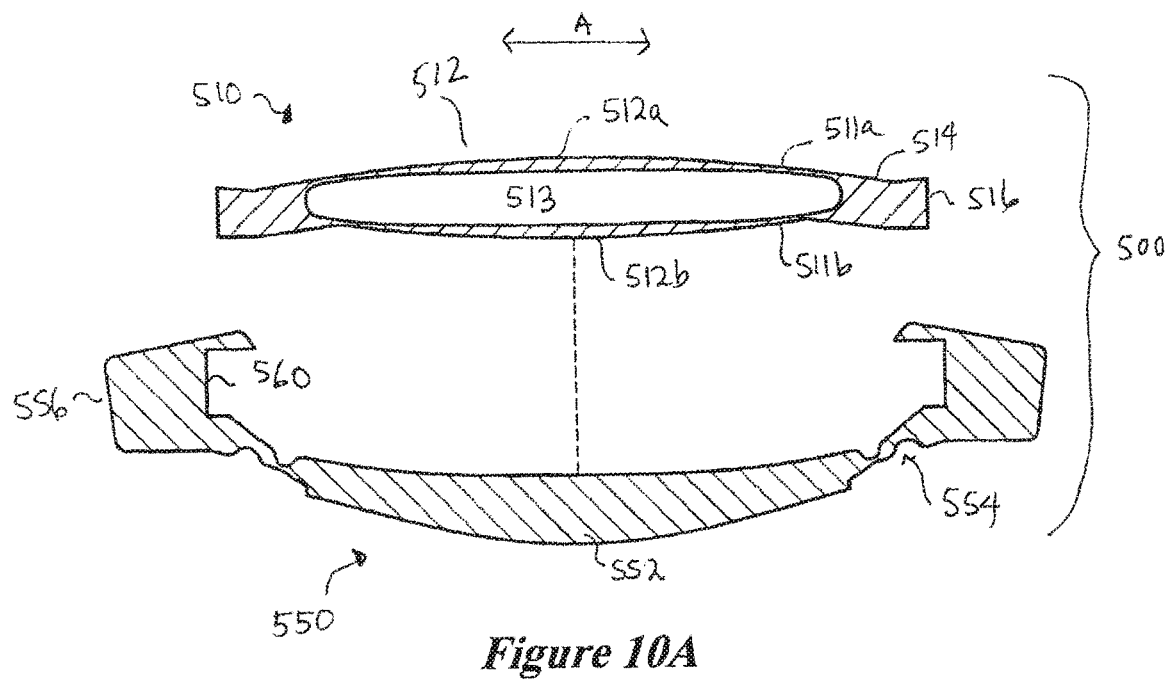
FIGS. 10A and 10B are exploded and coupled cross-sectional views of a further embodiment of a two-part accommodating IOL in which the power changing lens and the primary lens are coupled together.
Figure 10B:
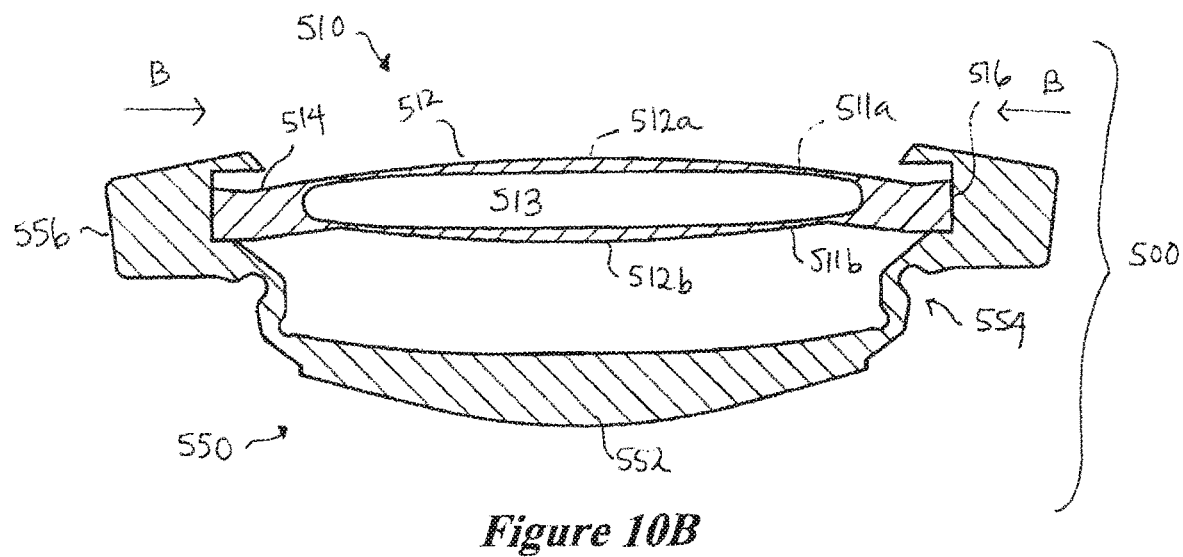

FIGS. 10A and 10B depict yet another embodiment of the two-part IOL device 500 comprising a power changing lens 510 and a fixed lens assembly 550. The power changing lens 510 comprises a enclosed lens chamber 512 defined by two opposing sides which change in curvature in response to radial forces applied to the periphery 516 of the haptic 514.

The two opposing surfaces are divided into central regions 512a, 512b and peripheral regions 511a, 511b. In a preferred embodiment, the central regions 512a, 512b have a gradually increasing thickness radially towards the center of the enclosed lens chamber 512 from the peripheral regions 511a, 511b. In a preferred embodiment, the center point of the central regions 512a, 512b has a thickness that is two times or more, preferably three times or more, and most preferably 4 times or more than the thickness of the peripheral region 511a, 511b. A fluid or gel 213 is contained between the opposing surfaces. In another preferred embodiment, the point of greatest thickness in the central region 512a, 512b and the point of least thickness in the peripheral region 511a, 511b is a ratio of 2:1 or greater, preferably 3:1 or greater, and most preferably 4:1 or greater. In a preferred embodiment, the thickness at the optical axis or the center of the central region 512a, 512b is about 200 microns and the thickness at the peripheral region 511a, 511b is about 50 microns. The increased thickness in the central region 512a, 512b is provided so as to prevent the opposing surfaces of the enclosed lens chamber 512 from buckling when it is deformed in response to accommodation. It is understood that in the various embodiments of the power lens depicted in the figures, the opposing sides preferably has the thickness profiles as described herein and depicted in FIGS. 4A-4F.

The fixed-lens assembly 550 comprises a fixed lens 552 that does not change in shape or curvature. An internal cavity is defined by the fixed lens 552 and the circumferential side walls 560. A circumferential hinge 554 provided on the fixed-lens assembly 550 peripherally of the fixed lens 552. The hinge 554 is disposed around the fixed lens 554 and thus permits the peripheral side wall 556 to be compressed radially-inwards in the direction of the arrows B to compress the power changing lens 510 at the contacting periphery 516. This, in turn, causes the opposing sides 512a, 512b to curve away from one another. Once the radial forces are no longer applied, the fixed lens assembly is resiliently biased to the expanded and unaccommodated state and the peripheral side wall expands in the direction as indicated by the arrows A.

Figure 11A:
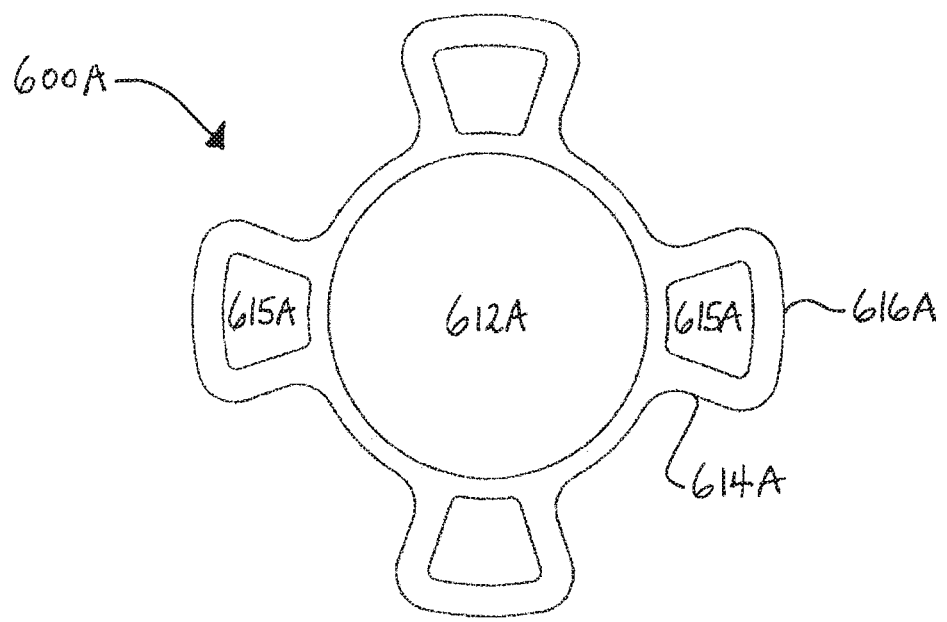
FIGS. 11A through 11F are top views of various alternate embodiments of the primary lens.
Figure 11B:
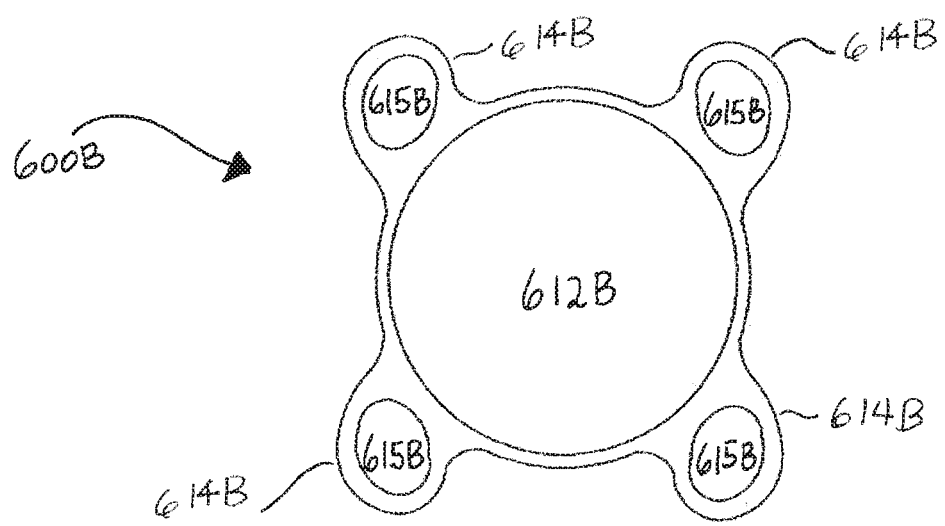
Figure 11C:
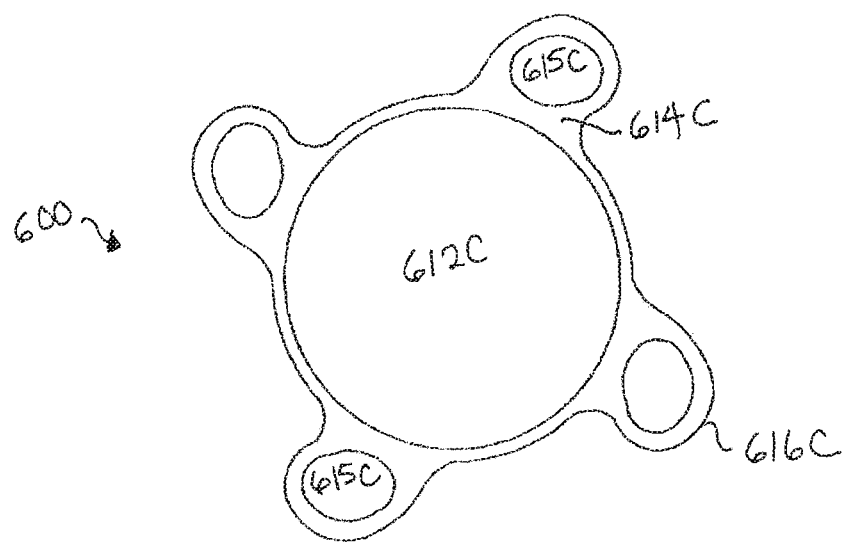

FIGS. 11A-11F depict various alternative embodiments of the fixed lens assemblies 600A-F that may be used in connection with any one of the fixed lens assembly described herein to form a two-part IOL device of the type described in FIGS. 1-3. As depicted in each of FIGS. 11A-11F, the haptics 614A-F are disposed in a symmetric matter so as to ensure centration of the power changing lens. FIG. 11A depicts a fixed lens assembly 600A having a lens 612A surrounded by four symmetrically disposed tabs 614A. The tabs each comprise an aperture 615A and an engaging edge 616A configured to engage the capsular bag of the patient's eye. FIG. 11B depict a similar arrangement of four haptics 614B, except that the haptics each have a rounded edge 616B and haptic pairs are pointed towards one another. FIG. 11C depict an arrangement of four haptics 614C, also having rounded edges 616C with the haptics being pointed in the same direction.

Figure 11D:
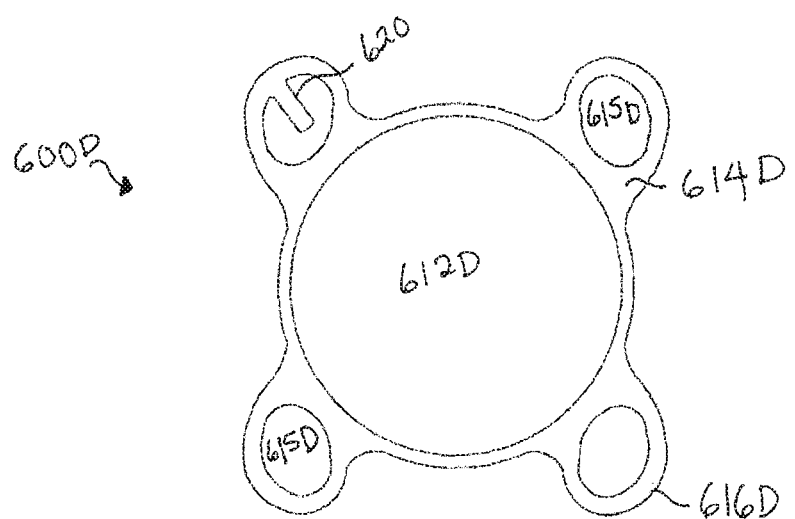

FIG. 11D depicts a fixed lens assembly 600D comprising a lens 612D and a plurality of haptics 614D each with an aperture 615D disposed therethrough. The haptics 614D further comprise a sizing finger 620 projecting from the outer engaging edge 616D. Implantation of the two-part IOL device typically requires the implantation of the fixed lens assembly first. Once the fixed lens assembly is implanted and positioned, the lens capsule walls may compress the engaging edge 616D and displace the sizing finger 620 toward the lens 612D. The extent to which the sizing finger 620 is displaced toward the lens 612D provides an indication as to the size of the patient's lens capsule so as to permit selection of the appropriately-sized power changing lens that is to be subsequently implanted in the patient's lens capsule.

Figure 11E:
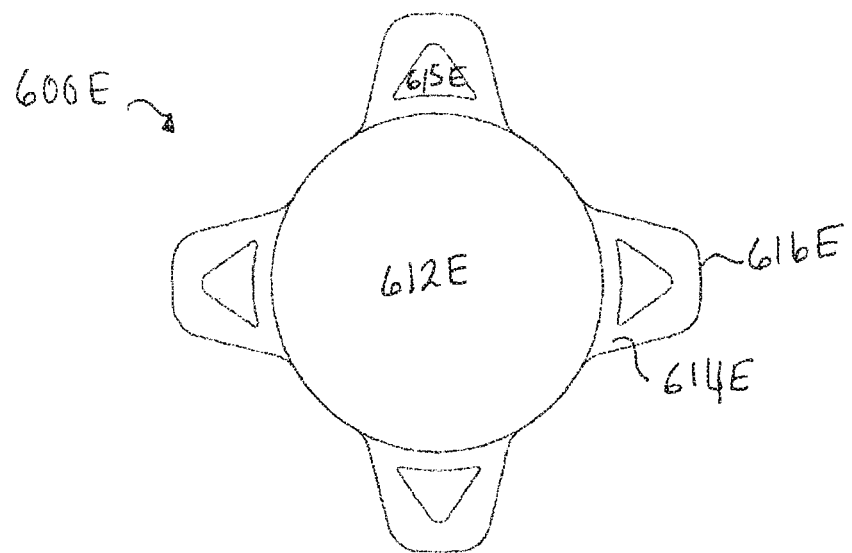

FIG. 11E depicts yet another fixed lens assembly 600E comprising four haptic tabs 614E each comprising a triangular shaped aperture 615E and a peripheral engaging edge 616E. The significance of the triangular shaped aperture 615E is to reduce the risk of snagging portions of the power changing lens during implantation.

Figure 11F:
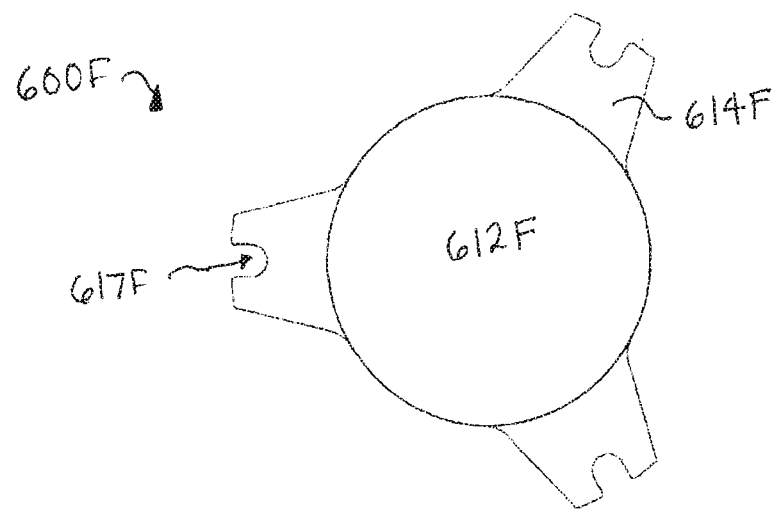

FIG. 11F depicts a further embodiment of the fixed lens assembly 600F comprising a lens 612F and three plate haptics 614F projecting therefrom. Because the configuration of the plate haptics 614F provides for a stiffer haptic, the fixed lens assembly 600F is preferably undersized relative to the lens capsule.

The invention described and claimed herein is not to be limited in scope by the specific preferred embodiments disclosed herein, as these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

The invention claimed is:

1. A two-part accommodating intraocular lens (IOL) device comprising:
   a power changing lens comprising an anterior surface, a posterior surface, an enclosed and fluid- or gel-filled lens cavity disposed between the anterior surface and the posterior surface, and a peripheral body disposed peripherally of the enclosed and fluid- or gel-filled lens cavity; and
   a base assembly comprising an optic centered on an optical axis and a haptic disposed peripherally of the optic, the haptic comprising:
      an inner circumferential surface engaging a circumferential edge of the peripheral body of the power changing lens; and
      a radially-compressible outer circumference spaced radially outward of the inner circumferential surface and configured to engage a capsular bag of a patient's eye, wherein the radially-compressible outer circumference surrounds the power changing lens and is uniformly radially compressible in response to ocular forces;
   wherein radial forces exerted on the radially-compressible outer circumference of the haptic are transmitted radially inward to the peripheral body of the power changing lens to cause an increase in curvature of at least one of the anterior and the posterior surfaces of the power changing lens.

2. The two-part accommodating IOL device of claim 1, wherein the anterior and the posterior surfaces of the power changing lens are spaced away from each other.

3. The two-part accommodating IOL device of claim 2, wherein an anterior surface of the optic is spaced away from the posterior surface of the power changing lens.

4. The two-part accommodating IOL device of claim 3, wherein the increase in curvature of the at least one of the anterior and the posterior surfaces occurs without contact between the optic and the posterior surface of the power changing lens.

5. The two-part accommodating IOL device of claim 4, wherein the increase in curvature of the at least one of the anterior and the posterior surfaces occurs without contact between the anterior and the posterior surfaces of the power changing lens.

6. The two-part accommodating IOL device of claim 3, further comprising a second cavity spacing apart the optic and the posterior surface of the power changing lens.

7. The two-part accommodating IOL device of claim 6, wherein the enclosed and fluid- or gel-filled lens cavity and the second cavity are not in fluid communication with the haptic.

8. The two-part accommodating IOL device of claim 6, wherein the second cavity is configured to permit a flow of aqueous fluid therein when the two-part accommodating IOL device is disposed in the patient's eye.

9. The two-part accommodating IOL device of claim 6, further comprising a plurality of holes around a periphery of the optic, the plurality of holes configured to permit a flow of aqueous body fluid into the second cavity.

10. The two-part accommodating IOL device of claim 1, wherein each of the anterior surface and the posterior surface of the enclosed and fluid-or gel-filled lens cavity comprises a central region centered on the optical axis and a peripheral region disposed peripherally of the central region.

11. The two-part accommodating IOL device of claim 10, wherein a thickness of the central region of the at least one of the anterior surface and the posterior surface of the power changing lens is at least two times greater than a thickness of the peripheral region of the at least one of the anterior surface and the posterior surface of the power changing lens.

12. The two-part accommodating IOL device of claim 10, wherein a thickness of the central region of the at least one of the anterior surface and the posterior surface of the power changing lens is at least three times greater than a thickness of the peripheral region of the at least one of the anterior surface and the posterior surface of the power changing lens.

13. The two-part accommodating IOL device of claim 10, wherein a thickness of the central region of the at least one of the anterior surface and the posterior surface of the power changing lens is at least four times greater than a thickness of the peripheral region of the at least one of the anterior surface and the posterior surface of the power changing lens.

14. The two-part accommodating IOL device of claim 1, wherein the base assembly further comprises a plurality of radial protrusions disposed over an anterior side of the peripheral body of the power changing lens when the power changing lens is disposed in the base assembly.

15. The two-part accommodating IOL device of claim 1, wherein the haptic further comprises circumferential hinges between the optic and the radially-compressible outer circumference.

16. The two-part accommodating IOL device of claim 1, wherein the power changing lens is entirely contained within the radially-compressible outer circumference of the base assembly.

17. The two-part accommodating IOL device of claim 1, wherein the optic is disposed posteriorly of the haptic.

18. The two-part accommodating IOL device of claim 1, wherein the optic is disposed posteriorly of a posterior side of the haptic.

19. A two-part accommodating intraocular lens (IOL) device comprising:
   a power changing lens comprising an anterior surface, a posterior surface, an enclosed and fluid- or gel-filled lens cavity disposed between the anterior surface and posterior surface, and a peripheral body disposed peripherally of the enclosed and fluid- or gel-filled lens cavity; and
   a base assembly comprising an optic intersected by an optical axis and a haptic disposed peripherally of the optic, the haptic comprising:
      an inner circumferential surface engaging a circumferential edge of the peripheral body of the power changing lens; and
      a radially-compressible outer circumference spaced radially outward of the inner circumferential surface and configured to engage a capsular bag of a patient's eye, wherein the radially-compressible outer circumference surrounds the power changing lens and is uniformly radially compressible in response to ocular forces;
   wherein radial forces exerted on the radially-compressible outer circumference of the haptic are transmitted radially inward to the peripheral body of the power changing lens to cause an increase in curvature of the anterior surface of the power changing lens.

20. The two-part accommodating IOL device of claim 19, further comprising a second cavity spacing apart the optic and the posterior surface of the power changing lens, the second cavity configured to permit a flow of aqueous fluid therein when the two-part accommodating IOL device is disposed in the patient's eye.

* * * * *